(12) United States Patent
Huang et al.

(10) Patent No.: US 8,580,738 B2
(45) Date of Patent: Nov. 12, 2013

(54) METHODS FOR TREATMENT OF REPERFUSION INJURY AND OTHER CARDIAC CONDITIONS

(75) Inventors: Ming-He Huang, League City, TX (US); Yochai Birnbaum, Houston, TX (US); Barry F. Uretsky, Fort Smith, AR (US)

(73) Assignee: The Board of Regents of the University of Texas System, Austin, TX (US)

( * ) Notice: Subject to any disclaimer, the term of this patent is extended or adjusted under 35 U.S.C. 154(b) by 675 days.

(21) Appl. No.: 12/598,131

(22) PCT Filed: Apr. 30, 2008

(86) PCT No.: PCT/US2008/062026
§ 371 (c)(1),
(2), (4) Date: Apr. 1, 2010

(87) PCT Pub. No.: WO2008/134727
PCT Pub. Date: Nov. 6, 2008

(65) Prior Publication Data
US 2011/0130334 A1    Jun. 2, 2011

Related U.S. Application Data

(60) Provisional application No. 60/926,919, filed on Apr. 30, 2007, provisional application No. 60/943,416, filed on Jun. 12, 2007.

(51) Int. Cl.
*A61K 38/17*    (2006.01)
*A61K 38/08*    (2006.01)
*A61P 9/10*    (2006.01)
*A61P 9/00*    (2006.01)

(52) U.S. Cl.
USPC ......... 514/16.4; 514/21.3; 514/11.9; 514/334

(58) Field of Classification Search
USPC .............................. 514/16.4, 21, 3, 11, 9, 334
See application file for complete search history.

(56) References Cited

FOREIGN PATENT DOCUMENTS

| EP | 1 579 862 | 9/2005 |
|---|---|---|
| WO | WO 2004/005550 | 1/2004 |
| WO | WO 2005/037230 * | 4/2005 |
| WO | WO 2005/062864 | 7/2005 |
| WO | WO 2005/070444 * | 8/2005 |
| WO | WO 2008/134727 | 11/2008 |

OTHER PUBLICATIONS

Wu et al. (Acta Pharmacol. Sin. 2001, vol. 22, No. &, pp. 588-594).*
"Effects of beta-blocker therapy and phosphodiesterase inhibition on cardiac neurohormonal activation," retrieved from http://www.clinicaltrials.gov/ct2/show/NCT00348101?term=esmolo&rank=8, Jul. 6, 2006.
Brain et al., "Calcitonin gene-related peptide is a potent vasodilator," *Nature*, 313:54-6, 1985.
Chai et al., "The role of calcitonin gene-related peptide (CGRP) in ischemic preconditioning in isolated rat hearts," *Eur. J. Pharmacol.*, 531:246-53, 2006.
Huang et al., "An intrinsic adrenergic system in mammalian heart," *J. Clin. Invest.*, 98:1298-1303, 1996.
Huang et al., "Mediating delta-opioid-initiated heart protection via the beta2-adrenergic receptor: role of the intrinsic cardiac adrenergic cell," *Am. J. Physiol. Heart Circ. Physiol.*, 293:H376-H384, 2007.
Li et al., "Calcitonin gene-related peptide-induced preconditioning protects against ischemia-reperfusion injury in isolated rat hearts," *Eur. J. Pharmacol.*, 311:163-7, 1996.
Murry et al., "Preconditioning with ischemia: a delay of lethal cell injury in ischemic myocardium," *Circulation*, 74:1124-36, 1986.
Sidi et al., "Administration of milrinone before ischemia, in the presence of (β-blockade, to treat metabolic impairment and myocardial stunning in pigs," *Acta. Anaesthesiologica Scandinavica*, 52:397-405, 2008.
Sidi et al., "Treatment of ischaemic left ventricular dysfunction with milrinone or doubutamine administered during coronary artery stenosis in the presence of beta blockade in pigs," *British Journal of Anesthesia*, 97:799-807, 2006.
Staat et al., "Postconditioning the human heart," *Circulation*, 112:2143-48, 2005.
Vinten-Johansen et al., "Postconditioning: a simple, clinically applicable procedure to improve revascularization in acute myocardial infarction," *Circulation*, 112:2085-88, 2005.
Wu et al., "Effects of calcitonin gene-related peptide and BIBN4096BS on myocardial ischemia in anesthetized rats," *Acta. Pharmacol. Sin.*, 22:588-94, 2001.

* cited by examiner

*Primary Examiner* — Fereydoun G Sajjadi
*Assistant Examiner* — Anna Falkowitz

(57) ABSTRACT

The present invention discloses methods to prevent and treat cardiovascular disorders, hi certain aspects the methods are drawn to releasing endogenous calcitonin-gene related peptide from intrinsic cardiac adrenergic cells within the heart. In further aspects, a combination of a $\beta_2$ adrenergic receptor agonist ($\beta_2$-AR agonist) and a vasodilator can be used in treating reperfusion injury.

10 Claims, 10 Drawing Sheets

METHODS FOR TREATMENT OF REPERFUSION INJURY AND OTHER CARDIAC CONDITIONS

The present application is a national phase application under 35 U.S.C. §371 of International Patent Application PCT Application No. PCT/US2008/062026, filed Apr. 30, 2008, which claims the benefit of US Provisional Application No. 60/926,919, filed Apr. 30, 2007 and US Provisional Application No. 60/943,416, filed Jun. 12, 2007. The entire contents of these applications are incorporated by reference.

BACKGROUND OF THE INVENTION

I. Field of the Invention

Embodiments of this invention are directed generally to biology, medicine, and cardiology. In particular aspects, the invention is related to combination therapy for treating cardiac and cardiovascular disorders and conditions, such as reperfusion injury.

II. Background

Currently, there are 5 million American with congestive heart failure, with nearly 500,000 new cases being diagnosed every year. Because of the high total direct costs of care for heart failure, estimated at $10 billion to $38 billion per year, the Centers for Medicare and Medicaid Services targeted heart failure as the disease most worthy of cost-effective management. Improvement in heart failure treatment in terms of innovative pharmacological strategies are urgently needed in this heart failure epidemic era.

In addition, acute myocardial infarction (MI) is the leading killer in the Unite States accounting for 54% mortality of total cardiovascular disease-related death (2004 NHLBI Chartbook). Although reperfusion therapy during acute MI with percutaneous coronary intervention (PCI) or thrombolysis salvages myocardium that would ultimately die without reperfusion, rapidly restoring blood flow to myocardium can also cause lethal injury to vulnerable myocardial cells (i.e., reperfusion injury). The restoration of blood flow can lethally compromise oxygen-deprived cells. Reperfusion injury may offset the optimal salvage of myocardium achieved by PCI and/or thrombolysis. Over the last 20 years extensive research efforts have been devoted to develop therapeutic strategies to prevent reperfusion injury.

Intravenous infusion of synthetic calcitonin-gene related peptide has been shown to improve cardiac hemodynamic performance and improve heart failure (a chronic condition as contrasted to acute MI) symptoms in patients with advanced heart failure. Additionally, adrenomedullin has also been shown to augment cardiac performance and improve clinical symptoms in heart failure patients (Nagaya, 2000). However, i.v. infusion of synthetic CGRP or adrenomedullin have not been approved by FDA for clinical use.

There is a need for additional compositions and methods for the treatment of cardiac and cardiovascular disorders, reperfusion injury, and post-ischemia conditioning.

SUMMARY OF THE INVENTION

Reperfusion injury is an unresolved clinical problem associated with acute MI and other sources of ischemia. Unfortunately, there is no drug clinically available that can be given after the onset of acute MI for reducing reperfusion injury. Mobilization and/or administration of endogenous cardioprotective neurohormones or compounds may provide a novel therapeutic strategy for treating and/or limiting reperfusion injury. Intrinsic cardiac adrenergic cell (ICA cell)-based research has provided insights into mobilizing endogenous heart protective neurohormonal mechanisms from ICA cells or administering pharmaceuticals to provide similar effects of protecting tissue (e.g., myocardium) and facilitating functional recovery after ischemic events. The positive inotropism and peripheral vasodilation (afterload reduction) effects of calcitonin-gene related peptide and $\beta_2$-adrenergic receptor agonist make it an attractive new drug for clinical heart failure treatment.

In certain aspects, a combination of a P2 adrenergic receptor agonist ($\beta_2$-AR agonist) and a vasodilator can be used in treating, reducing, ameliorating, and/or preventing reperfusion injury. In certain aspects reperfusion injury is tissue infarction. In particular aspects, the vasodilator, e.g., exogenous CGRP or a CGRP receptor agonist, and a $\beta_2$-AR agonist can be administered (e.g., concomitantly in a mixture) to provide a more effective therapeutic strategy for reducing tissue damage after an ischemic event or during reperfusion of a tissue. In a further aspect, reperfusion injury is treated by ischemia-postconditioning of a target tissue.

"Ischemia-preconditioning" is the most frequent experimental model for reperfusion injury (Murry, 1986), but translation to the clinical arena has been challenging. The broad definition of ischemia-precondition is that of mobilizing endogenous cardioprotective mechanisms by administering short periods of decreased oxygenation and/or drug prior to the onset of MI can reduce infarct size during the reperfusion period. The major problem of ischemia-preconditioning has been that to reduce infarct size the preconditioning event or drug requires institution hours to days prior to MI onset. Thus, ischemia-preconditioning is clinically unrealistic, since patients arrive at the hospital already experiencing a MI.

"Ischemia-postconditioning" is a new concept aimed at therapy that can be delivered at the beginning of reperfusion during an acute MI to reduce reperfusion-injury. Currently, only percutaneous coronary catheter based strategy has shown clinical promise to achieve "mechanical" ischemia-postconditioning (Staat 2005, Vinten-Johansen 2005).

Embodiments of the invention include compositions and methods for combination therapy with $\beta_2$-adrenergic receptor ($\beta_2$-AR) agonist (e.g., terbutaline) and vasodilators (e.g., calcitonin gene-related peptide (CGRP) or CGRP receptor agonist) conferring infarct-size reduction when delivered at the beginning of reperfusion. This invention is based on the inventors' discovery that simultaneous stimulation of cardiac $\beta_2$-AR and CGRP-receptors via mobilizing endogenous epinephrine and CGRP release from ICA cells confers potent infarct-size-limiting effect during experimental MI.

In certain aspects, the invention includes methods of treating reperfusion injury comprising administering a composition comprising a $\beta_2$-adrenergic receptor agonist and a vasodilator in an amount sufficient to reduce, limit, ameliorate, or otherwise treat reperfusion injury to a tissue, such as, but not limited to, myocardium. In further aspects, the vasodilator is calcitonin gene-related peptide (CGRP), a CGRP receptor agonist, adrenomedullin, or amylin. In still a further aspect, the vasodilator is CGRP receptor agonist, such as CGRP, and/or a catecholamine, with the exception of norepinephrine. In still other aspects, the $\beta_2$-adrenergic receptor agonist is a terbutaline, albuterol, biterol, epinephrine, dobutamine, dopamine, formoterol, isoproterenol, levalbuterol, metaproterenol, salmeterol, or ritodrine. In a certain aspect, the $\beta_2$-adrenergic receptor agonist is terbutaline. In yet another aspect, the composition comprises terbutaline and CGRP or a mimetic thereof. The $\beta_2$-adrenergic receptor agonist and other small molecule pharmaceuticals described herein (including small molecule vasodilators) can be administered at a dose of at least, at most, or about 1, 2, 5, 10, 25, 50, 75, 100, 150, 200, 250, 300, 350, 400, 450 ng or µg/kg to 500 ng or µg/kg, including all values and ranges there between. In certain aspects, the vasodilator can be administered at a dose of at least, at most, or about 0.1, 0.5, 1, 2, 5, 10, 20, 30, 40, 50, 60, 70, 80, 90 ng/kg to 100 ng/kg, including all values and ranges there between. In still a further aspect of the invention a δ-opioid agonist can be administered before, during, or after a composition comprising $\beta_2$-adrenergic receptor agonist and a vasodilator. The δ-opioid agonist can be administered at a dose of at least, at most, or about 1, 2, 5, 10, 25, 50, 75, 100, 150, 200, 250, 300, 350, 400, 450 ng or µg/kg to 500 ng or µg/kg, including all values and ranges there between.

In certain embodiments, the step of administering is performed during and/or after an ischemic event and at least before, during or after reperfusion or reperfusion therapy of a target tissue. In certain embodiments, the $\beta_2$-adrenergic receptor agonist and the vasodilator are administered separately. In other aspects, the $\beta_2$-adrenergic receptor agonist and the vasodilator are administered in a single formulation. The composition comprising the $\beta_2$-adrenergic receptor agonist and the vasodilator can be administered within at least, at most, or about 5, 10, 20, 30, 40, 50 minutes to 1, 2, 3, 4, 5, 6, 7, 8, 9, 10, 11, 12, 13, 14, 15, 16, 17, 18, 19, 20, 21, 22, 23, 24 hours before, during, or after an ischemic event, i.e., the reduction or cessation in blood flow to a target tissue, and/or before, during, or after reperfusion or reperfusion therapy. Reperfusion can be initiated by artificial or natural processes. Artificial processes include mechanical reperfusion, chemical reperfusion, and the like. Mechanical reperfusion, for example, can be by angioplasty and other procedures utilizing an intravascular catheter. Chemical reperfusion includes, but is not limited to administration of thrombolytics, such as alterplase, anistreplace, reteplase, streptokinase, tenecteplase, and urokinase to name a few. In a particular aspect, the $\beta_2$-adrenergic receptor agonist and the vasodilator are administered within at least, at most, or about 30 minutes of an ischemic event, e.g., MI, or reperfusion, e.g., angioplasty, etc. Typically, administration of the compositions of the invention is typically intravascularly, intraosseusly, intraarterially, transdermally, transmucosally, or by inhalation. In certain aspects, the compositions of the invention are administered through the arteries supplying blood to a particular target tissue, e.g., a coronary artery. The composition can be administered intravascularly, intravenously, and/or intraarterially. In certain aspects, the compositions are administered by an intracoronary route.

Other aspects of the invention include methods of treating reperfusion injury in a subject in need such treatment, comprising the step of administering to a subject who has had, is having, or is at risk of having an ischemic event an amount of a composition comprising $\beta_2$-adrenergic receptor agonist and a vasodilator sufficient to reduce reperfusion injury in an ischemic tissue.

In certain embodiments of the present invention, there is provided a method of treating an individual at risk or with an established cardiovascular disorder. Such a method comprises the step of administering to the individual a pharmacologically effective amount of a composition that induces synthesis and/or release of calcitonin-gene related peptide from intrinsic cardiac adrenergic cells within the heart of the individual. An "effective amount" of a compound can be formulated with a pharmaceutically acceptable carrier to form a pharmaceutical composition before being administered for treatment of a disease. "An effective amount" or "pharmacologically effective amount" refers to the amount of compound that is required to confer therapeutic effect on the treated subject, e.g., reduced reperfusion injury, etc. Effective doses will also vary, as recognized by those skilled in the art, depending on the route of administration, the excipient usage, and the optional co-usage with other therapeutic treatments.

In another embodiment of the present invention, there is provided a method of reducing myocardial infarct size in an individual. Such a method comprises administering to the individual a pharmacologically effective amount of a composition that induces synthesis and/or release of calcitonin-gene related peptide from intrinsic cardiac adrenergic cells within the heart of the individual. In certain aspects the released calcitonin-gene related peptide induces an anti-apoptotic effect, thereby reducing myocardial infarct size in the individual. In certain aspects the composition comprises a δ-opioid agonist or a $\beta_2$-adrenergic receptor agonist. The δ-opioid agonist or $\beta_2$-adrenergic receptor agonist can be administered at a dose of at least, at most, or about 1, 2, 5, 10, 25, 50, 75, 100, 150, 200, 250, 300, 350, 400, 450 ng or µg/kg to 500 ng or µg/kg, including all values and ranges there between.

In yet another embodiment of the present invention there is provided a method of reducing drug-induced cardiomyopathy in an individual. Programmed cell death or apoptosis is a phenomenon implicated as one of the key mechanisms underlying the pathogenesis of chemotherapy, i.e., doxorubicin-induced cardiomyopathy. When the cardiotoxic effects of doxorubicin in patients treated for advanced cancer were studied, an incidence of >5% of doxorubicin-induced cardiomyopathy was reported at a dose of 501-550 mg/m$^2$ body surface area, increasing to 30% at over 550 mg/m$^2$ (Lefrak et al., 1973). In animal studies, intravenous calcitonin-gene related peptide infusion or stimulation of myocardial calcitonin-gene related peptide receptors by calcitonin-gene related peptide-receptor agonist, adenomedullin, exerted a potent anti-apoptotic effect against cardiomyocyte death induced by chemotherapy drug, doxorubicin (Tokudome, 2002) or oxidative stress (Sueur, 2005). This effect suggests that calcitonin-gene related peptide may exert myocyte protection against doxorubicin-induced myocardial damage during doxorubicin chemotherapy.

Methods comprise administering to the individual a pharmacologically effective amount of a composition that induces synthesis and/or release of calcitonin-gene related peptide from intrinsic cardiac adrenergic cells within the heart of the individual, where the released calcitonin-gene related peptide reduces apoptotic effect of the drug, thereby reducing the drug-induced cardiomyopathy in the individual.

In still yet another aspect of the present invention, there is a method of protecting heart from cardiovascular disease. Such a method comprises contacting an intrinsic cardiac adrenergic cell within the heart with a composition that induces synthesis and/or release of calcitonin-gene related peptide from intrinsic cardiac adrenergic cells such that the released calcitonin-gene related peptide reduces myocardial infarct size, improves cardiac hemodynamic performance, improves heart failure symptoms, reduces apoptotic effect of cardiotoxic drug or combinations thereof, thereby protecting the heart from cardiovascular disease.

In certain aspects CGRP inducing catecholamine is epinephrine or dobutamine. In a further aspect, the released calcitonin-gene related peptide and/or catecholamines reduces myocardial infarct size, improves cardiac hemodynamic performance, improves heart failure symptoms, and/or reduces apoptotic effect of a cardiotoxic drug. In certain aspects norepinephrine can be specifically excluded from the genus catecholamines. The CGRP inducing composition comprises a δ-opioid agonist or a $\beta_2$-adrenergic receptor agonist. δ-opioid agonist include, but is not limited to (D-pen$^2$, D-pen$^5$)-enkephalin (DPDPE), [D-Pen$^{25}$]-enkephalin, D-Ala2-D-Leu5-enkephalin and a deltorphin. $β_2$-adrenergic receptor agonist include, but are not limited to epinephrine, metaproterenol, terbutaline, albuterol, formoterol, levalbuterol, salmeterol, bitolterol or ritodrine. Cardiovascular disorder includes, but is not limited to myocardial ischemia, myocardial dysfunction, drug-induced cardiomyopathy, decompensated heart failure, or hypertension. In certain aspects the drug-induced cardiomyopathy is a chemotherapeutic agent. The chemotherapeutic agent can be doxorubicin (Adriamycin) or daunorubicin (Cerubidine). The CGRP inducing composition can be administered prior to, concurrent with or subsequent to the administration of the drug.

A treated individual can be suffering from chronic stable angina, acute coronary syndrome or is experiencing myocardial infarction.

In another aspect of the present invention, there is a method of identifying compounds useful in treatment of a cardiovascular disorder. Such a method comprises contacting intrinsic cardiac adrenergic cells with the compound and measuring the levels of calcitonin-gene related peptide released in the presence and absence of the compound. This is followed by comparing the levels of calcitonin-gene related peptide released in the presence of the compound with the levels of calcitonin-gene related peptide released in the absence of the compound. In certain aspects, an increase in the levels of calcitonin-gene related peptide in the presence of a compound is indicative that the compound is useful in the treatment of cardiovascular disorder.

The composition described herein can be administered prior to, concurrent with, or subsequent to another drug (for instance, a chemotherapeutic agent). The effect of co-administration with the composition is to reduce cardiotoxic effect of the drug without reducing, ameliorating, eliminating, or otherwise interfering with any cytotoxic, cytostatic, apoptotic or other killing or inhibitory therapeutic effect of the drug.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

As used herein, the term "contacting" refers to any suitable method of bringing the composition described herein into contact with a intrinsic cardiac adrenergic cell. In vitro or ex vivo this is achieved by exposing the intrinsic cardiac adrenergic cell to the composition in a suitable medium. For in vivo applications, any known method of administration is suitable as described herein.

As used herein, the term "agonist" or "antagonist" means a molecular entity of natural, semi-synthetic or synthetic origin that either activates or blocks, stops, inhibits, and/or suppresses the calcitonin-gene related peptide pathway. For instance, the agonist will activate the pathway while the antagonist will block, stop, inhibit, and/or suppress a pathway.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A and 1B demonstrate the co-expression of calcitonin-gene related peptide and TH immunoreactivity in an intrinsic cardiac adrenergic cell. The TH-expressing sympathetic nerve fiber (FIG. 1B, arrow) is seen in this locus. FIG. 1C is the overlay image of FIG. 1A and FIG. 1B showing the confinement of calcitonin-gene related peptide and TH immunoreactivity within the same cell. Insert in FIG. 1C is the magnified intrinsic cardiac adrenergic cell image. FIGS. 1D and 1E demonstrate the coexpression of calcitonin-gene related peptide mRNA (FIG. 1D) and TH immunoreactivity (FIG. 1E) in another intrinsic cardiac adrenergic cell. FIG. 1F is the overlay image of FIG. 1D and FIG. 1E showing confinement of calcitonin-gene related peptide mRNA and TH within the same cell. Insert in FIG. 1F is the magnified image of intrinsic cardiac adrenergic cell. No calcitonin-gene related peptide-containing nerve ending was seen intramyocardially.

DETAILED DESCRIPTION OF THE INVENTION

Figure 1A:
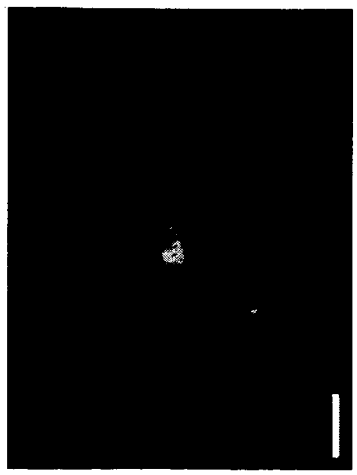
FIGS. 1A-1F show co-localization of calcitonin-gene related peptide immuno-reactivity, calcitonin-gene related peptide mRNA and tyrosine hydroxylase (TH) in intrinsic cardiac adrenergic cells in human left ventricular myocardial tissue.
Figure 1B:
Figure 1C:
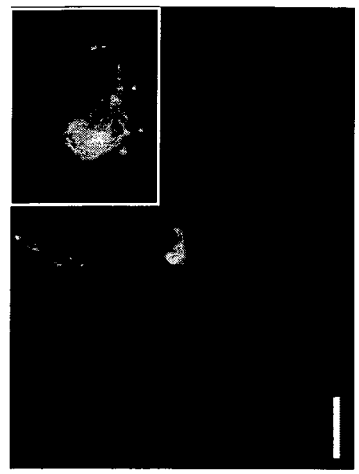
Figure 1D:
Figure 1E:
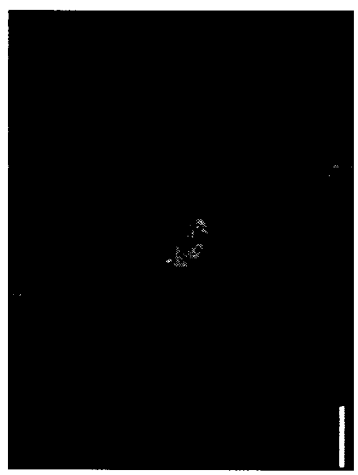
Figure 1F:
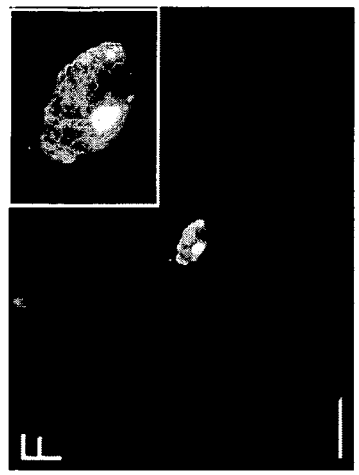

Despite the increase in the incidence of cardiovascular disease such as heart failure and the high total direct costs of care of patients with this ailment, synthetic CGRP or adrenomedullin, which have shown to augment cardiac performance and improve clinical symptoms in patients with heart failure have still not been approved by FDA. Thus, there is an urgent need to develop pharmacological strategies that are safe and effective in the treatment of such disease.

Timely reperfusion salvages myocardium from tissue injury after prolonged ischemia. However, restoration of blood flow to ischemic myocardium may exaggerate injury that is not present at the end of ischemia. This reperfusion injury is primarily expressed as contractile and coronary vascular endothelial dysfunction, upregulation of adhesion molecules on the endothelium, and transendothelial migration of inflammatory cells into the parenchyma, edema, infarction, and apoptosis. Embodiments of the present invention provide additional compositions and methods for treating, ameliorating, reducing, and/or limiting this reperfusion injury as well as other cardiac and cardiovascular disorders.

The intrinsic cardiac adrenergic (ICA) cell synthesizes and releases epinephrine, an endogenous $β_2$-adrenoreceptor ($β_2$-AR) agonist that exerts potent myocardial infarct-size-limiting effect via $β_2$-AR stimulation in a rat model (Huang et al., 2007). The inventors have described methods and compositions using ICA cell-derived epinephrine for heart disease treatment. Recently, the inventors have discovered that the ICA cell synthesizes and releases a neuropeptide, namely calcitonin gene-related peptide (CGRP), in human and rat hearts. The prepro-form of human CGRP has an amino acid sequence of RIIAQKRACDTATCVTHRLAGLLSRSG-GVVKNNFVPTNVGSKAFGRRRRDLQ A (SEQ ID NO:1). Aspects of the invention include peptides of at least, at most, or about 5, 6, 7, 8, 9, 10, 11, 12, 13, 14, 15, 16, 17, 18, 19, 20, 21, 22, 23, 24, 25, 2, 27, 28, 29, 30, 31, 32, 33, 34, 35, 36, 37, 38, 39, 40, 41, 42, 43, 44, 45, 46, 47, 48, 49, 50, 51, 52, and 53 contiguous amino acids of SEQ ID NO:1 or mimetic or variant thereof. CGRP derived from ICA cells exerts infarct-size-limiting effect in rat heart. The broad implications of intrinsic cardiac adrenergic cells have been linked to developmental biology, cardiac impulse generation and conduction, blood pressure regulation, post-transplanted heart function and heart protection against myocardial infarction (Huang et al., 2007).

In certain aspects of the invention, endogenous or exogenous $β_2$-AR agonist and CGRP receptor agonist confer synergistic infarct-size-limiting effect in a MI model whereas blockade of cardiac $β_2$-AR or CGRP-receptors each increases the infarct size compared with the control group (saline infusion). Dual blockade of $\beta_2$-AR and CGRP-receptors increases the infarct size additively compared to its individual receptor blockade. This result indicates that endogenous epinephrine and CGRP exert basal tonic infarct-size-limiting effect.

The inventors have demonstrated that tonic infarct-size-limiting effect exerted by endogenous epinephrine and CGRP can be greatly augmented (56% reduction in infarct size compared with saline control) following the stimulation of ICA cells with $\delta$-opioid agonist. Endogenous epinephrine and CGRP mutually augment the infarct-size-limiting effect.

The inventors contemplate that simultaneously enhanced epinephrine and CGRP release following $\delta$-opioid stimulation of ICA cells confers profound infarct-size-limiting-effect, which is additive to the individual epinephrine- or CGRP-mediated effect. This finding serves as the foundation for the development of new drugs which can specifically target ICA cells mobilizing epinephrine and CGRP production or pharmaceutical formulations providing $\beta_2$-AR agonist and vasodilators directly to myocardium providing protection to myocardium from reperfusion injury. In certain aspects, a combination therapy with $\beta_2$-AR and vasodilator (e.g., CGRP-receptor agonists) confers maximum infarct-size-reduction, particularly a composition comprising both a $\beta_2$-AR and a vasodilator.

Similar to the finding that endogenous epinephrine and CGRP exert synergistic infarct-size-reduction, the inventors have demonstrated that intravenous infusion of $\beta_2$-AR agonist (e.g., terbutaline) and a vasodilator (e.g., CGRP) 20-min before the onset of coronary artery occlusion exerts profound infarct-size-reduction in rats. Furthermore, when delivered 20-min after the onset of coronary artery ligation (post-ischemic conditioning), the dual therapy confers profound infarct-size-reduction.

The magnitude of infarct-size-limiting effect provided by combination therapy of $\beta_2$-AR agonist (e.g., terbutaline) and a vasodilator (e.g., CGRP) is impressive even delivered in a delayed fashion (i.e., 30-min after the onset coronary artery occlusion). This phenomenon has particular clinical relevance, since most patients with acute heart attack have already experience coronary artery occlusion for 30-min to 1-hr or longer before arriving at a hospital. The cardioprotective effect demonstrated here can revolutionize the concept and management of MI treatment. In other aspects, the compositions and methods can prevent or rescue heart muscle damage in patients suffering from acute MI.

I. Reperfusion Injury

Ischemia is a deficiency of blood or blood flow in a part typically due to functional constriction or actual obstruction of a blood vessel. Such a deficiency result in an infarct, an area of cell death in a tissue due to local ischemia resulting from obstruction of circulation to the area, most commonly by a thrombus, embolus, or ruptured or obstructing atherosclerotic plaque. When the constriction or obstruction is removed and blood flow restored reperfusion occurs. Although blood flow is restored, the reperfusion can also result in adverse effects including cellular swelling and necrosis, apoptosis, edema, hemorrhage, the no-reflow phenomenon, and tissue damage by free oxygen radicals.

Reperfusion injury to the heart is accompanied by the upregulation and post-translational modification of a number of proteins normally involved in regulating cell cycle progression. Disclosed are methods and compositions for reducing reperfusion injury including, but not limited to reduction or limitation of infarct size. In certain aspects, the methods are equally appropriate for use in reducing injury following stroke including, but not limited to ischemic strokes (including strokes resulting from cerebral thrombosis, cerebral embolism, and atrial fibrillation), hemorrhagic strokes (including strokes resulting from aneurysm and arteriovenous malformation), and transient ischemic attack), reducing infarct size following pulmonary infarction, reducing renal ischemia injury, reducing ischemic/reperfusion injury occurring during cardiac surgery where a heart lung machine is used such as coronary artery bypassing, and reducing reperfusion injury occurring during the preservation of organs for transplant.

Generation of abundant oxygen free radicals during early reperfusion has been implicated as a major player in the pathogenesis of tissue injury associated with reperfusion. The burst of oxygen-derived free radicals occurs within the first minute and peaks at 4 to 7 min after reperfusion; increased free radical generation is still detectable during later periods of reperfusion. Superoxide anions have been implicated in lipid peroxidation of biological membranes, triggering adhesion molecule expression on endothelium, and subsequent initiation of neutrophil and endothelial cell interactions. Both in vivo and in vitro studies have shown that oxygen free radicals are potent stimuli for the rapid upregulation of P-selectin and ICAM-1 on endothelium as well as initiation of acute inflammation and subsequent recruitment of neutrophils in ischemic myocardium.

II. Related Therapeutic Methods and Compositions

Disclosed are compositions and methods of reducing reperfusion injury in a subject in need thereof comprising administering to the subject a composition comprising a $\beta_2$-AR agonist (e.g., terbutaline) and/or a vasodilator (e.g., CGRP). One manifestation of reducing reperfusion injury is reducing or limiting or ameliorating infarct size. Therefore, disclosed herein are methods of reducing infarct size following a reperfusion event in a subject comprising administering to the subject the inventive compositions that inhibit, reduce, limit, or ameliorate an infarct.

It is understood that there are many known causes of reperfusion injury. For example, a reperfusion injury can result from ischemia/reperfusion event such as myocardial ischemia, myocardial reperfusion, subendocardial ischemia, Takayasu's arteritis, including but not limited to (ischemic strokes (including strokes resulting from cerebral thrombosis, cerebral embolism, and atrial fibrillation), hemorrhagic strokes (including strokes resulting from aneurysm and arteriovenous malformation), and transient ischemic attack), pulmonary infarction, hypoxia, retinal ischemia, renal ischemia, cardiac surgery where a heart lung machine is used such as coronary artery bypassing, and preservation of organs for transplant. Thus, also disclosed herein are methods of reducing reperfusion injury comprising administering a composition comprising a $\beta_2$-AR agonist (e.g., terbutaline) and/or a vasodilator (e.g., CGRP), wherein the reperfusion injury occurs following an ischemia/reperfusion event that includes, but is not limited to myocardial ischemia, myocardial reperfusion, subendocardial ischemia, Takayasu's arteritis, stroke, ischemia strokes, cerebral thrombosis, cerebral embolism, atrial fibrillation, hemorrhagic strokes, aneurysm and arteriovenous malformation, transient ischemia attack, pulmonary infarction, hypoxia, retinal ischemia, renal ischemia, ischemic/reperfusion event occurring during cardiac surgery where a heart lung machine is used such as coronary artery bypassing, and ischemic/reperfusion events occurring during the preservation of organs for transplant.

By "treatment" and "treating" is meant the medical management of a subject with the intent to cure, ameliorate, stabilize, or prevent a disease, condition, or disorder. This term includes active treatment, i.e, treatment directed specifically toward the improvement of a disease, condition, or disorder. Treatment and treating also include causal treatment, i.e., treatment directed toward removal of the cause of the associated disease, condition, or disorder. In addition, this term includes palliative treatment, i.e., treatment designed for the relief of symptoms rather than the curing of the disease, condition, or disorder; preventative treatment, i.e., treatment directed to minimizing or partially or completely inhibiting the development of the associated disease, condition, or disorder; and supportive treatment, i.e., treatment employed to supplement another specific therapy directed toward the improvement of the associated disease, condition, or disorder. It is understood that treatment, while intended to cure, ameliorate, stabilize, or prevent a disease, condition, or disorder, need not actually result in the cure, ameliorization, stabilization, or prevention. It is understood and herein contemplated that "treatment" does not necessarily refer to a cure of the disease or condition nor a complete prevention of infarct, but can involve, for example, an improvement in the outlook of an reperfusion injury. The effects of treatment can be measured or assessed as described herein and as known in the art as is suitable for the disease, condition, or disorder involved (e.g., MI, etc.). Such measurements and assessments can be made in qualitative and/or quantitative terms. Thus, for example, characteristics or features of a disease, condition, or disorder and/or symptoms of a disease, condition, or disorder can be reduced to any effect or to any amount.

Also, for example, treating reperfusion injury can comprise any method or the administration of any combination of a $\beta_2$-AR agonist (e.g., terbutaline) and a vasodilator (e.g., CGRP) that affects tissue damage resulting from reperfusion or ameliorates the degree of or potential for tissue injury associated with an ischemia/reperfusion event.

"Reducing," "reduce," or "reduction" in the context of a disease or condition herein refers to a decrease in the cause, symptoms, or effects of a disease or condition. Therefore, in the disclosed methods, "reducing" can refer to a 10%, 20%, 30%, 40%, 50%, 60%, 70%, 80%, 90%, or 100% decrease, or any value or range there between, in the amount of injury due to reperfusion including but not limited to infarct size.

It is contemplated that the disclosed methods and compositions can be used to reduce reperfusion injury following an ischemic event. Thus, for example, disclosed are methods of reducing reperfusion injury in a subject in need thereof comprising administering to the subject a composition comprising a $\beta_2$-AR agonist (e.g., terbutaline) and/or a vasodilator (e.g., CGRP) and/or a δ-opioid agonist, wherein the agents are administered at least, at most or about 0.1, 0.5, 1, 1.5, 2, 2.5, 5, 6, 7, 8, 9, 10, 11, 12, 13, 14, 15, 16, 17, 18, 19, 20, 21, 22, 23. or 24 hours, including all values and ranges there between, before or following a reperfusion event. It is understood that the more quickly the composition can be administered following the reperfusion event, the less the likelihood of injury and subsequently the greater the potential reduction in infarct size and benefit to the subject. Thus, disclosed herein are methods wherein the agent is administered within 24, 12, 6, 2, 1 hour(s) to 30, 15, 10, 5 minutes before or following reperfusion. It is understood that administration of the agent can occur at any time between 5 minutes and 24 hours before or following the ischemia/reperfusion event. It is also understood that ischemia and reperfusion are not only physiologically different events, but do not necessarily occur at the same time. As ischemia refers to deficiency of blood to a part typically due to a thrombus or embolus and reperfusion injury results when the obstruction or constriction is removed, it is possible and desirable to reduce reperfusion injury during or after the ischemia/reperfusion event. Thus, for example, a composition comprising a $\beta_2$-AR agonist (e.g., terbutaline) and a vasodilator (e.g., CGRP) could be administered during the ischemia or alternatively after the ischemia, but before reperfusion has occurred, or alternatively after the ischemia and at the time of or during reperfusion. Thus, disclosed herein are methods wherein the agents are administered during the ischemia and/or reperfusion event.

In certain embodiments the composition comprising a $\beta_2$-AR agonist (e.g., terbutaline) and a vasodilator (e.g., CGRP) is administered before the ischemia and/or reperfusion event. Thus, it is contemplated that individuals at risk for or having a history of ischemia/reperfusion events can decrease the risk of further necrosis in future events by administration of a $\beta_2$-AR agonist (e.g., terbutaline) and a vasodilator (e.g., CGRP) composition prophylactically, which also includes prior to, during, or after catheterization or other medical procedures. It is also understood that many ischemia/reperfusion events have early warning symptoms preceding the actual event which when recognized can allow the subject to seek immediate treatment. Even if there is ischemic/reperfusion injury caused by future ischemia/reperfusion events, it is contemplated that the prophylactic administration of $\beta_2$-AR agonist (e.g., terbutaline) and a vasodilator (e.g., CGRP) composition will reduce infarct size. For example, disclosed herein are methods of reducing ischemia/reperfusion injury in a subject in need thereof (having, had, or at risk of having an ischemic/reperfusion event) comprising administering to the subject a $\beta_2$-AR agonist (e.g., terbutaline) and a vasodilator (e.g., CGRP) composition that, wherein the composition is administered at least 30 minutes before the ischemia/reperfusion event. Thus, disclosed herein are methods wherein the agent is administered 15, 30 minutes, 1, 2, 6, 12, 24 hour(s), 2, 3 days, 1. or 2 weeks or any time point in between before the ischemia/reperfusion event.

In particular aspects, compositions of the invention can be administered before, during, and/or after percutaneous transluminal coronary angioplasty, vascular grafts in surgical revascularization (before removal of the aortic cross-clamp in on-pump cardiac surgery), removal of the target vessel ligature during off-pump coronary artery bypass graft surgery, organ transplantation or other procedures of events that impede blood flow to myocardium or other organs or tissues.

It is also understood and herein contemplated that the secretory response of ICA cells can be used to screen for agents that can reduce ischemia/reperfusion injury. Thus, embodiments of the invention include methods of screening for an agent that reduces ischemia/reperfusion injury comprising administering an agent to a subject (e.g., rodent or other model), inducing ischemia/reperfusion, and measuring the levels of epinephrine and/or CGRP, wherein an increase in the level(s) relative to a control indicates an agent that reduces ischemia/reperfusion injury. These screening methods may also be used to screen for an agent(s) that reduces infarct size following reperfusion comprising administering an agent to a subject, inducing ischemia/reperfusion, and measuring the levels of epinephrine and/or CGRP, wherein an increase in the level(s) relative to a control indicates an agent that can reduce infarct size. It is understood that the subject can be any mammal including but not limited to mouse, rat, rabbit, guinea pig, cow, horse, pig, cat, dog, monkey, chimpanzee, or human. It is also understood that epinephrine and/or CGRP can be assessed by any method known by the skilled artisan or developed in the future to assess protein activity such as Western Blot or ELISA assay. Candidate compounds include, but are not limited to Class of β2-Adrenergic Agonists: terbutaline, albuterol, biterol, epinephrine, dobutamine, dopamine, formoterol, isoproterenol, levalbuterol, metaproterenol, salmeterol, ritodrine, and analogs, mimics, and derivatives thereof; δ-Opioid Agonists: morphine, DPDPE, (−)-TAN-67 (SB205607), [D-Ala2,Glu4]-Deltorphin, DSLET, SNC80. and analogs, mimics, and derivatives thereof; Nitrates: any forms of nitroglycerine (sublingual, transdermal ointment, oral spray, intravenous), isosorbide dinitrate, isosorbide mononitrate, and analogs, mimics, and derivatives thereof.

In certain embodiments, the present invention discloses a novel approach to prevent and/or treat cardiovascular disorders. In this regard, the present invention discloses regulatory mechanisms of calcitonin-gene related peptide synthesis and release from intrinsic cardiac adrenergic cells. This disclosure provides for pharmacological manipulation (i.e., new drug development) specifically targeting intrinsic cardiac adrenergic cells. Furthermore, mobilizing endogenous calcitonin-gene related peptide production and release from intrinsic cardiac adrenergic cells within the human heart may serve as a safer and effective intervention in the prevention and treatment of cardiovascular disorders including, but not limited to, myocardial ischemia, myocardial dysfunction, drug-induced myocardial dysfunction, congestive heart failure or hypertension.

The present invention further demonstrates that human intrinsic cardiac adrenergic cells release significant amounts of calcitonin-gene related peptide. The constitutive synthesis and release of CGRP in human intrinsic cardiac adrenergic cells provides a foundation for pharmacological targeting of calcitonin-gene related peptide production specifically in intrinsic cardiac adrenergic cells. Additionally, δ-opioid agonist such as DPDPE and $β_2$-adrenergic receptor agonist, epinephrine upregulated the expression of the calcitonin-gene related peptide gene and increase CGRP release. This sustained calcitonin-gene related peptide gene upregulation and augmented release has important implication since it can lead to sustained calcitonin-gene related peptide synthesis and release in the heart. This property may potentially eliminate the continuous exogenous calcitonin-gene related peptide administration for the therapeutic purpose of cardiovascular diseases.

In addition to the sustained expression of the calcitonin-gene related peptide gene, the present invention also demonstrates that DPDPE induced CGRP and epinephrine release reduced the myocardial infarct size. Thus infarct-size-limiting effect exerted by endogenous calcitonin-gene related peptide and epinephrine may be due to their anti-apoptotic effect. Thus, the findings discussed herein may contribute significantly against ischemia-reperfusion injury and have clinical implications in several cardiovascular diseases including, but not limited to, myocardial ischemic protection, heart failure or doxorubicin-induced myopathy.

Myocardial ischemic protection: Since intrinsic cardiac adrenergic cell-derived calcitonin-gene related peptide exerts significant myocardial infarct size reduction in an animal model, the mobilization of calcitonin-gene related peptide synthesis and/or release by stimulating intrinsic cardiac adrenergic cells with δ-opioid receptor agonists is contemplated to provide an effective intervention to reduce infarct size. One theory is that this effect is via its antiapoptotic effect in humans. The inventors have identified δ-opioid receptor expressed in intrinsic cardiac adrenergic cells (Huang et al., 2007). The expression of δ-opioid receptor by intrinsic cardiac adrenergic cells provides a basis for pharmacological manipulation of endogenous CGRP regulation. Further, methods to mobilize calcitonin-gene related peptide from intrinsic cardiac adrenergic cells may be useful anti-ischemic agent for patients with chronic stable angina, acute coronary syndrome and during acute myocardial infarction.

Heart failure (heart failure): Mobilizing calcitonin-gene related peptide and epinephrine release from intrinsic cardiac adrenergic cells instead of intravenous infusion of synthetic calcitonin-gene related peptide or adrenomedullin can serve as a safer and more effective alternative for calcitonin-gene related peptide based heart failure therapy. δ-opioid stimulation of ICA cells can increase ventricular contractile function, providing novel therapeutic approach for heart failure.

Doxorubicin-induced cardiomyopathy: There is no specific drug available for the prevention and treatment of doxorubicin-induced cardiomyopathy. Experimental evidence has demonstrated that exogenously applied calcitonin-gene related peptide reduces the apoptosis induced by doxorubicin. It is likely that mobilization of endogenous calcitonin-gene related peptide production and release from intrinsic cardiac adrenergic cells (for instance, using δ-opioid agonists), may provide an effective antiapoptotic approach to prevent or reverse the course of doxorubicin-induced cardiomyopathy in cancer patients receiving doxorubicin-based chemotherapy.

The present invention is directed to a method of treating an individual at risk or with established cardiovascular disorder, comprising the steps of: administering to the individual a pharmacologically effective amount of a composition that induces synthesis and/or release of calcitonin-gene related peptide from intrinsic cardiac adrenergic cells within heart of the individual. In general, the released calcitonin-gene related peptide and epinephrine may reduce myocardial infarct size, may improve cardiac hemodynamic performance, may improve heart failure symptoms, may reduce apoptotic effect of a cardiotoxic drug or combinations thereof. The composition that is administered in this method may comprise a δ-opioid agonist or a $β_2$-adrenergic receptor agonist. Representative examples of a useful δ-opioid agonist may include but is not limited to (D-Pen$^2$, D-Pen$^5$)-enkephalin (DPDPE), [D-pen$^{25}$]-enkephalin, a deltorphin or D-Ala2-D-Leu5-enkephalin. The $β_2$-adrenergic receptor agonist may include but is not limited to epinephrine, metaproterenol, terbutaline, albuterol, formoterol, levalbuterol, salmeterol, bitolterol or ritodrine. Additionally, the cardiovascular disorder that the individual has or is at risk of developing may include, but is not limited to myocardial ischemia, myocardial dysfunction, drug-induced cardiomyopathy or hypertension. Furthermore, the drug in the drug-induced cardiomyopathy may include but is not limited to a chemotherapeutic agent. Examples of the chemotherapeutic agent may include but is not limited to doxorubicin (Adriamycin) or daunorubicin (Cerubidine).

The present invention is also directed to a method of reducing myocardial infarct size in an individual, comprising: administering to the individual a pharmacological effective amount of a composition that induces synthesis and release of calcitonin-gene related peptide from intrinsic cardiac adrenergic cells within the heart of the individual, where the released calcitonin-gene related peptide induces an anti-apoptotic effect, thereby reducing myocardial infarct size in the individual. The composition administered in such a method may comprise a δ-opioid agonist or a $β_2$-adrenergic receptor agonist. Examples of the δ-opioid agonist may include but is not limited to (D-Pen$^2$, D-Pen$^5$)-enkephalin (DPDPE), [D-pen$^{25}$]-enkephalin, a deltorphin or D-Ala2-D-Leu5-enkephalin. The β2-adrenergic receptor agonist may include but is not limited to epinephrine, metaproterenol, terbutaline, albuterol, formoterol, levalbuterol, salmeterol, bitolterol or ritodrine. The individual who may benefit from this method may include but is not limited to one who is suffering from chronic stable angina, acute coronary syndrome, or is experiencing or has experienced myocardial infarction.

The present invention is further directed to a method of reducing drug-induced cardiomyopathy in an individual, comprising: administering to the individual a pharmacological effective amount of a composition that induces synthesis and/or release of calcitonin-gene related peptide from intrinsic cardiac adrenergic cells within the heart of the individual, where the released calcitonin-gene related peptide reduces apoptotic effect of the drug, thereby reducing the drug-induced cardiomyopathy in the individual. The composition in such a method may be administered prior to, concurrent with, or subsequent to the administration of the drug. Examples of the drug may include but is not limited to a chemotherapeutic agent. Additionally, examples of the chemotherapeutic agent may include but is not limited to doxorubicin (Adriamycin) or daunorubicin (Cerubidine).

The present invention is still further directed to a method of protecting the heart from cardiovascular disease, comprising: contacting intrinsic cardiac adrenergic cells within the heart with a composition that induces synthesis and/or release of calcitonin-gene related peptide from intrinsic cardiac adrenergic cells such that the released calcitonin-gene related peptide reduces myocardial infarct size, improves cardiac hemodynamic performance, improves heart failure symptoms, reduces apoptotic effect of a cardiotoxic drug or combinations thereof, thereby protecting the heart from cardiovascular disease. The composition used in this method may comprise a δ-opioid agonist or a $β_2$-adrenergic receptor agonist. Examples of the δ-opioid agonist may include but is not limited to (D-Pen$^2$, D-Pen$^5$)-enkephalin (DPDPE), [D-pen$^{25}$]-enkephalin, a deltorphin or D-Ala2-D-Leu5-enkephalin and those of the β2-adrenergic receptor agonist may include but is not limited to epinephrine, metaproterenol, terbutaline, albuterol, formoterol, levalbuterol, salmeterol, bitolterol, or ritodrine.

The present invention is also directed to a method of identifying compounds useful in treatment of cardiovascular disorder, comprising: contacting intrinsic cardiac adrenergic cells with the compound; measuring the levels of calcitonin-gene related peptide released in the presence and absence of the compound; and comparing the levels of calcitonin-gene related peptide released in the presence of the compound with the levels of calcitonin-gene related peptide released in the absence of the compound, where an increase in the levels of calcitonin-gene related peptide in the presence of the compound is indicative that the compound is useful in the treatment of cardiovascular disorder. This method may further comprise screening the compound for anti-ischemic activity in a myocardial ischemia-reperfusion model. Such a screening step may comprise comparing infarct size in the presence of the compound with infarct size in the presence of a compound known to increase the infarct size, where a reduction in the infarct size in the presence of the compound is indicative that the compound has anti-ischemic activity. The examples of cardiovascular disorder that the compound may treat may include but is not limited to myocardial ischemia, myocardial dysfunction, drug-induced cardiomyopathy or hypertension.

A. Calcitonin Gene-Related Peptide (CGRP)

CGRP is a neuropeptide distributed in the central and peripheral sensory nervous systems. CGRP is a potent vasodilator that has important implication in blood pressure regulation (Brain, 2004). The cardiac effects of CGRP include an inotropic effect on isolated human (Saetrum et al., 2000) and animal ventricular muscle (Miyauchi et al., 1988; Van Gelderen et al., 1995) and isolated rat ventricular myocytes (Huang et al., 1999). Several clinical trials have demonstrated the benefit of CGRP in improving cardiac output in chronic heart failure (CHF) patients (Anand et al., 1991. Dobois-Rande et al., 1992. Gennari et al., 1990. Shekhar et al., 1991). Intravenous CGRP infusion improves heart function in advanced CHF patients (Gennari et al., 1990). In dilated cardiomyopathic patients CGRP infusion exerts dose-dependent increase in cardiac output associated with reduced pulmonary arterial wedge pressure (Anand et al., 1991).

CGRP is a potent vasodilator of human coronary arteries (Gulbenkian, 1993; Hasbak 2003). Intravenous CGRP infusion significantly dilates small coronary arteries at normal and atheromatous sites (Uren et al., 1993; Lundman et al., 1991) delaying the onset of myocardial ischemia during exercise in patients with stable angina (Uren et al., 1993). CGRP also mediates myocardial ischemic preconditioning via its infarct-size-limiting effect (Lu et al., 2001; Wolfrum et al., 2005).

In the human heart, CGRP-expressing nerve endings derived from paravertebral dorsal root ganglia are only scarcely distributed to epicardial coronary arteries. They are absent in the deeper layers of ventricular myocardium (Chow et al., 1993). It is unclear whether any type of heart cell produces CGRP thereby exerting direct cardiac modulation. The inventors have discovered that ICA cells synthesize and release CGRP. The inventors also contemplate that CGRP and epinephrine co-released from ICA cells confer synergistic protection against myocardial ischemia. Furthermore, the inventors contemplate that synergistic cardioprotection mediated by endogenous CGRP and epinephrine can be simulated by combination therapy with exogenous CGRP and $β_2$-AR agonist.

Calcitonin-gene related peptide (CGRP) is a 37 amino acid neuropeptide identified in 1982. The calcitonin-gene related peptide mRNA appears to predominate in the nervous system. Calcitonin-gene related peptide exerts a range of biological effects on tissues including those associated with gastrointestinal, cardiac, respiratory, endocrine and central nervous system. Calcitonin-gene related peptide also exerts profound cardiovascular effects.

Calcitonin-gene related peptide exerts significant myocardial protection against ischemia via two mechanisms. First, calcitonin-gene related peptide is a potent systemic and coronary arterial vasodilator (Brain and Grant, 2004). Calcitonin-gene related peptide induces concentration-dependent relaxation of isolated human coronary arteries (Gulbenkian et al., 1993). Intravenous infusion of calcitonin-gene related peptide significantly dilates small coronary arteries at normal and atheromatous stenotic sites (Uren et al., 1993; Lundman et al., 2000). It also delays onset of myocardial ischemia during treadmill exercise testing in patients with chronic stable angina (Uren et al., 1993). Secondly, calcitonin-gene related peptide mediates myocardial ischemic preconditioning (Luo et al., 2004; Wolfrum et al., 2005). Endogenous calcitonin-gene related peptide has infarct-size limiting effect during myocardial infarction, an effect mimicking ischemia preconditioning.

B. β2-adrenergic Receptor (β2-AR) Agonist

β2-AR agonists act on the β2-adrenergic receptor causing smooth muscle relaxation resulting in dilation of bronchial passages, vasodilation in muscle and liver, relaxation of uterine muscle and release of insulin. All clinically approved β2 agonists are available in inhaler form (either metered-dose inhalers, which aerosolize the drug, or dry powder which can be breathed in).

Salbutamol (known as albuterol in the U.S.) also comes in a liquid form for nebulization, which is more commonly used in emergency rooms than inhalers. Salbutamol and terbutaline are also both available in oral forms.

In addition, several of these medications are available in intravenous forms including both salbutamol and terbutaline. It can be used in this form in severe cases of asthma, but more commonly it is used to suppress premature labor because it also relaxes uterine muscle, thereby inhibiting contractions.

$\beta$2-AR agonists can typically be divided into two groups: (1) short-acting and (2) long-acting. Short-acting $\beta$2 agonists include, but are not limited to, salbutamol (albuterol), levalbuterol, terbutaline, pirbuterol, procaterol, metaproterenol, fenoterol, or bitolterol mesylate. Long-acting $\beta$2 agonists include, but are not limited to, salmeterol, formoterol, or bambuterol.

C. Vasodilators

Vasodilation is a process where blood vessels in the body develop a wider internal diameter (dilate) following the relaxation of the smooth muscle in the vessel wall. This effect will reduce systemic arterial pressure (blood pressure). Vasodilation also occurs in superficial blood vessels of warm-blooded animals when the ambient environmental temperature increases as a method of heat dissipation, i.e., this process diverts the flow of heated blood to the skin of the animal, where heat can be more easily released into the atmosphere. The opposite physiological process is called vasoconstriction.

A vasodilator is a substance that causes vasodilation. Several vasodilators are used as drugs which may, for example, allow blood to flow more easily around a clot. Vasodilators include, but are not limited to CGRP, adrenomedullin, amylin, adenosine (e.g., adenocard and alpha blockers), amyl nitrite and other nitrites, L-Arginine, atrial natriuretic peptide (ANP), bradykinin, ethanol, endothelium-derived hyperpolarizing factor (EDHF), histamine, niacin (nicotinic acid), nitric oxide, glyceryl trinitrate, isosorbide mononitrate, isosorbide dinitrate, pentaerythritol tetranitrate (PETN), sodium nitroprusside, PDE5 inhibitors (sildenafil, tadalafil, vardenafil), platelet activating factor (PAF), prostacyclin (PGI2) and other prostaglandins, tetrahydrocannabinol (THC), theobromine, and papaverine.

III. Pharmaceutical Formulations and Delivery

Methods of the present invention include the delivery of an effective amount of a $\beta_2$-AR agonist (e.g., terbutaline) and/or a vasodilator (e.g., CGRP receptor agonist) and/or a $\delta$-opioid agonist composition. An "effective amount" or "pharmacologically effective amount" of a pharmaceutical composition, generally, is defined as that amount sufficient to detectably and repeatedly achieve the stated desired result, for example, to ameliorate, reduce, minimize or limit the extent of the disease or its symptoms (i.e., reperfusion injury). Other more rigorous definitions may apply, including elimination, eradication or cure of disease or condition. The interrelationship of dosages for animals and humans (based on milligrams per square meter of body surface) is described by Freireich et al. (1966). Body surface area may be approximately determined from height and weight of the patient. See, e.g., Scientific Tables (1970).

A. Administration

In certain embodiments, it is desired to limit, reduce, or ameliorate infarct size and/or reverse or reduce reperfusion injury. The routes of administration will vary, naturally, with the location and nature of the lesion or site to be targeted, and include, e.g., regional, parenteral, intravenous, intramuscular, and/or systemic administration and formulation. Direct injection or injection into the vasculature or the vessels to and from and within an organ or tissue is specifically contemplated for target areas. Local, regional, or systemic administration also may be appropriate.

Multiple injections delivered as a single dose comprise at least, at most or about 0.01 to 0.5 ml volumes or more. Compositions of the invention may be administered in multiple injections to a targeted site.

Continuous administration also may be applied where appropriate, for example, where a catheter or intrvenous (IV) system is used to administer the present treatment or as an adjunct to another standard treatment for ischemia and it associated complications. Delivery via syringe or catherization is specifically contemplated. Such continuous perfusion may take place for a period from about 0.5-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs.

Treatment regimens may vary as well and often depend on target site, subject condition, and health and age of the patient. Certain conditions will require more aggressive treatment. The clinician will be best suited to make such decisions based on the known efficacy and toxicity (if any) of the therapeutic formulations or methods.

Treatments may include various "unit doses." A unit dose is defined as containing a predetermined quantity of a therapeutic composition(s). The quantity to be administered, and the particular route and formulation, are within the skill of those in the clinical arts. A unit dose need not be administered as a single injection but may comprise continuous infusion over a set period of time. A unit dose may conveniently be described in terms of μg, ng, or mg of component. Alternatively, the amount specified may be the amount administered per subject weight (typically kg) or as the average daily, average weekly, or average monthly dose.

Components can be administered to a subject in a dose or doses of about or of at least about 0.5, 1, 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 pg, ng, μg or mg, or more, or any range derivable therein. Alternatively, the amount specified may be the amount administered as the average daily, average weekly, or average monthly dose, or it may be expressed in terms of ng/kg, μg/kg, or mg/kg, where kg refers to the weight of the subject or patient. In other embodiments, the amount specified is any number discussed above but expressed as mg/m$^2$ (with respect to target, organ, or tissue surface area).

Toxicity and therapeutic efficacy of active ingredients can be determined by standard pharmaceutical procedures, e.g., for determining LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

B. Injectable Compositions and Formulations

In some embodiments, the method for the delivery of a $\beta_2$-AR agonist (e.g., terbutaline) and a vasodilator (e.g., CGRP) composition is via intraarterial or intravenous administration. Injection of a $\beta_2$-AR agonist (e.g., terbutaline) and a vasodilator (e.g., CGRP) composition may be delivered by syringe or catheter or any other method used for injection of a solution, as long as the $\beta_2$-AR agonist (e.g., terbutaline) and a vasodilator (e.g., CGRP) composition and any associated components can pass through the particular gauge of needle or device required for injection or intravascular delivery.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, mixtures thereof, and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In certain formulations, a water-based formulation is employed while in others, it may be lipid- or oil-based. In particular embodiments of the invention, a composition comprising one or more $\beta_2$-AR agonist (e.g., terbutaline) and/or vasodilator (e.g., CGRP) is in a water-based formulation. In other embodiments, the formulation is lipid based.

For aqueous solutions, the solution should be suitably buffered if necessary. A liquid diluent is typically rendered isotonic with sufficient saline or glucose. These aqueous solutions are especially suitable for intravenous administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

As used herein, a "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human.

The $\beta_2$-AR agonist (e.g., terbutaline) and vasodilator (e.g., CGRP) compositions are administered in a manner compatible with the dosage formulation, and in such amount as will be therapeutically effective. The quantity to be administered depends on the subject to be treated, including, e.g., the length and severity of an ischemic event. Precise amounts of active ingredient required to be administered depend on the judgment of the practitioner. Suitable regimes for initial administration and subsequent administration are also variable, but are typified by an initial administration followed by other administrations. Such administration may be systemic, as a single dose, continuous over a period of time spanning 10, 20, 30, 40, 50, 60 minutes, and/or 1, 2, 3, 4, 5, 6, 7, 8, 9, 10, 11, 12, 13, 14, 15, 16, 17, 18, 19, 20, 21, 22, 23, 24 or more hours, and/or 1, 2, 3, 4, 5, 6, 7. days or more.

C. Combination Treatments

In certain embodiments, the compositions and methods of the present invention involve $\beta_2$-AR agonist (e.g., terbutaline) and vasodilator (e.g., CGRP) components. These compositions can be used in combination with a second therapy to enhance the effect of the therapy, or increase the therapeutic effect of another therapy being employed. These compositions would be provided in a combination effective to achieve the desired effect, such as the reperfusion of an ischemic area and/or the inhibition of ischemia/reperfusion injury. This process may involve contacting the target area with a $\beta_2$-AR agonist (e.g., terbutaline) and a vasodilator (e.g., CGRP) composition and/or a second therapy at the same or different time. This may be achieved by contacting the target area with one or more devices, compositions or pharmacological formulation that includes or more of the agents, or by contacting the target area or region with two or more distinct devices, compositions or formulations, wherein one composition provides (1) a $\beta_2$-AR agonist (e.g., terbutaline) and a vasodilator (e.g., CGRP); and/or (2) a second therapy. A second composition or method may be administered that includes mechanical manipulation, a chemotherapy, radiotherapy, surgical therapy, immunotherapy or gene therapy.

It is contemplated that one may provide a patient with the $\beta_2$-AR agonist (e.g., terbutaline) and vasodilator (e.g., CGRP) composition therapy and the second therapy simultaneously or within about 0.5 to 12 to 24 minutes or hours of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

In certain embodiments, a course of treatment will last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 minutes, hours, days or more. It is contemplated that one agent may be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89. and/or 90. any combination thereof, and another agent is given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89. and/or 90. or any combination thereof. Within a single day (24-hour period), the patient may be given one or multiple administrations of the agent(s). Moreover, after a course of treatment, it is contemplated that there is a period of time at which no treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Various combinations may be employed, for example $\beta_2$-AR agonist (e.g., terbutaline) and vasodilator (e.g., CGRP) composition therapy is "A" and a second therapy is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

Administration of any compound or therapy of the present invention to a patient will follow general protocols for the administration of such compounds or therapy, taking into account the toxicity or potential complications, if any, of the other agent or therapy. Therefore, in some embodiments there is a step of monitoring toxicity or complications that are attributable to combination therapy. It is expected that the treatment cycles would be repeated as necessary. It also is contemplated that various standard therapies, as well as surgical intervention, may be applied in combination with the described therapy.

Disclosed are the components to be used to prepare the disclosed compositions to be used within the methods disclosed herein. These and other materials are disclosed herein, and it is understood that when combinations, subsets, groups, etc. of these materials are disclosed that specific reference to an individual and collective combination and permutation of these compounds may not be explicitly disclosed, each is specifically contemplated and described herein. For example, if a particular $\beta_2$-AR agonist (e.g., terbutaline) or vasodilator (e.g., CGRP) is disclosed and discussed and a number of modifications that can be made to a number of molecules are discussed, specifically contemplated is each and every combination and permutation of $\beta_2$-AR agonist (e.g., terbutaline) or vasodilator (e.g., CGRP) and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

IV. Variants of B2-AR Agonist and Vasodilators

It is also understood that one way to define any known variants and derivatives or those that might arise, of the disclosed compounds and/or peptides herein is through defining the variants and derivatives in terms of homology or identity to specific known sequences or compounds. For example SEQ ID NO. 1 sets forth a particular sequence of a CGRP. Specifically disclosed are variants of these and other peptides herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the stated sequence. Those of skill in the art readily understand how to determine the homology of two proteins or nucleic acids. For example, the identity can be calculated after aligning the two sequences.

Protein or peptide variants and derivatives are well understood to those of skill in the art and can involve amino acid sequence modifications or mimetics. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein or peptide sequence. Typically, no more than about from 2 to 6 residues are deleted at any one site within the molecule. These variants ordinarily are prepared by site specific mutagenesis of nucleotides in the DNA encoding the protein, thereby producing DNA encoding the variant, and thereafter expressing the DNA in recombinant cell culture. Amino acid substitutions are typically of single residues, but can occur at a number of different locations at once; insertions usually will be on the order of about from 1 to 10 amino acid residues; and deletions will range about from 1 to 30 residues.

Substitutional variants are those in which at least one residue has been removed and a different residue inserted in its place. Substantial changes in function or immunological identity are made by selecting substitutions that are less conservative, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one having a substantially smaller side chain, e.g., glycine, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides or peptide provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g., Arg, is accomplished for example by deleting one of the basic residues or substituting one by glutaminyl or histidyl residues.

Molecules can be produced that resemble peptides, but which are not connected via a natural peptide linkage. For example, linkages for amino acids or amino acid analogs can include CH$_2$NH—, —CH$_2$S—, —CH$_2$—CH$_2$—, —CH=CH— (cis and trans), —COCH$_2$—, —CH(OH) CH$_2$—, and —CHH$_2$SO— (These and others can be found in Spatola (1983a); Spatola (1983b); Morley (1980); Hudson et al., (1979) (—CH$_2$NH—, CH$_2$CH$_2$—); Spatola et al. (1986) (—CHH$_2$—S); Hann (1982) (—CH—CH—, cis and trans); Almquist et al. (1980) (—COCH$_2$—); Jennings-White et al. (1982) (—COCH$_2$—); EP 45665 CA (1982) (—CH(OH) CH$_2$—); Holladay et al. (1983) (—C(OH)CH$_2$—); and Hruby (1982) (—CH$_2$—S—); each of which is incorporated herein by reference. A particular non-peptide linkage is —CH$_2$NH—. It is understood that peptide analogs can have more than one atom between the bond atoms, such as β-alanine, γ-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch, 1992), incorporated herein by reference).

It is understood that the compositions disclosed herein have certain functions, such as a β$_2$-AR agonist (e.g., terbutaline) and a vasodilator (e.g., CGRP receptor agonist). Disclosed herein are certain structural requirements for performing the disclosed functions, and it is understood that there are a variety of structures which can perform the same function which are related to the disclosed structures, and that these structures will ultimately achieve the same result, for example activation of β$_2$-AR receptor or vasodilation.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

V. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Immunohistochemical Identification of CGRP and CGRP mRNA in Human Intrinsic Cardiac Adrenergic Cells Immunohistochemical study coupled with in situ hybridization technique was performed in surgically discarded left ventricular tissues from human hearts. It was observed that the intrinsic cardiac adrenergic cells expressed calcitonin-gene related peptide immunoreactivity and expressed calcitonin-gene related peptide mRNA in situ in human left ventricular tissue (FIG. 1A-1F). While sympathetic nerve endings were frequently identified, no CGRP-containing sensory nerve endings were identified in the left ventricular myocardium.

Example 2

CGRP Release from Intrinisic Cardiac Adrenergic Cells in Human Heart

Figure 2:
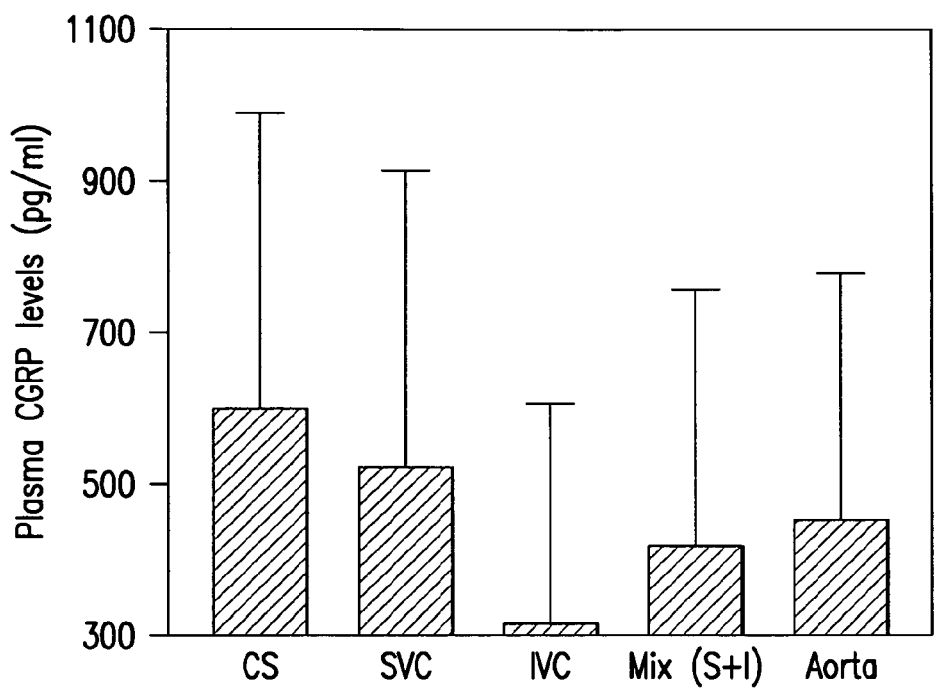
FIG. 2 shows significantly elevated plasma CGRP levels in the coronary sinus (CS), superior vena cava (SVC), inferior vena cava (IVC), calculated mixed SVC-IVC (Mix (S+I)) and aorta (n=6). The mean posttransplantation duration in these patients is 25.8 months (ranging from 11 to 60 months). **: p<0.01.

Human heart is innervated by calcitonin-gene related peptide-containing afferent nerves primarily supplying epicardial coronary arteries. The transplanted human heart remains calcitonin-gene related peptide-afferent nerve denervated up to 63 months post-transplantation (Wharton, 1990), thereby lacking nerve-derived calcitonin-gene related peptide. Without afferent nerve innervation, the intrinsic cardiac adrenergic cells can independently release calcitonin-gene related peptide in human heart. It was observed herein that intrinsic cardiac adrenergic cells spilled over significantly high amount of calcitonin-gene related peptide intracardiacally than those in the central veins and aorta (FIG. 2). This indicates that intrinsic cardiac adrenergic cells constitute a primary source for cardiac calcitonin-gene related peptide synthesis and release independent of afferent nerve innervation.

Example 3

Regulation of CGRP Gene-Expression and Release in Intrinsic Cardiac Adrenergic

Figure 3:
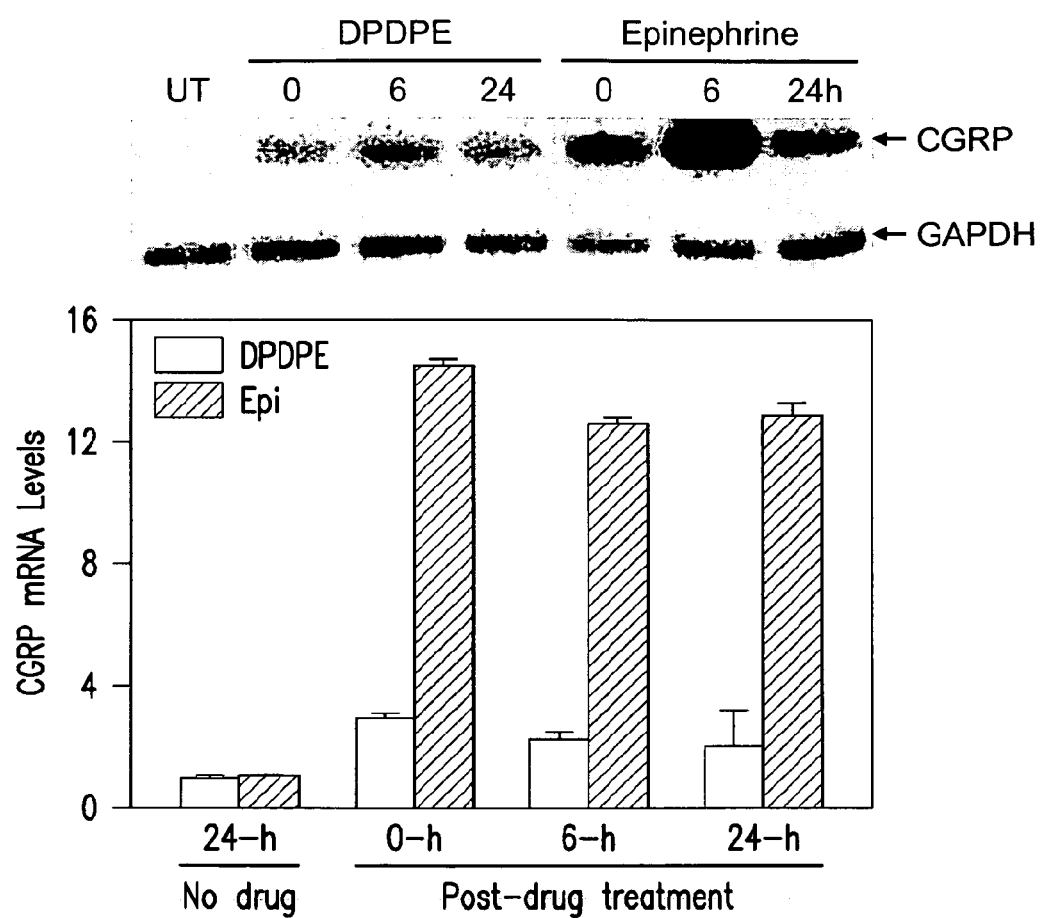
FIG. 3 shows the up-regulation of calcitonin-gene related peptide mRNA in isolated rat intrinsic cardiac adrenergic cells following the treatment with DPDPE (100 nM for 60 min) or epinephrine (1 μmol for 60 min) at three different post-treatment times by RT-PCR. 0-h represents immediately after 60-min drug treatment. 6-h and 24-h represent 6 and 24 hrs after 60 min drug treatment, respectively. Epi: epinephrine. UT: DPDPE-untreated. Total RNA loading in each lane is equivalent as shown by the amount of GAPDH mRNA. Bar graph: Quantitative real-time PCR shows 2-fold and 14-fold increase in calcitonin-gene related peptide mRNA following 60-min treatment of DPDPE and epinephrine, respectively.

The present invention also demonstrated that δ-opioid agonist DPDE and β$_2$-adrenergic receptor agonist, epinephrine upregulate calcitonin-gene related peptide gene expression in rat intrinsic cardiac adrenergic cells (FIG. 3). While δ-opioid agonist modestly increases calcitonin-gene related peptide mRNA levels, epinephrine is a very potent stimulant increasing calcitonin-gene related peptide mRNA levels by 14 fold. This robust gene regulatory effect lasted for 24 hrs following a brief 60-min of epinephrine treatment.

Figure 4:
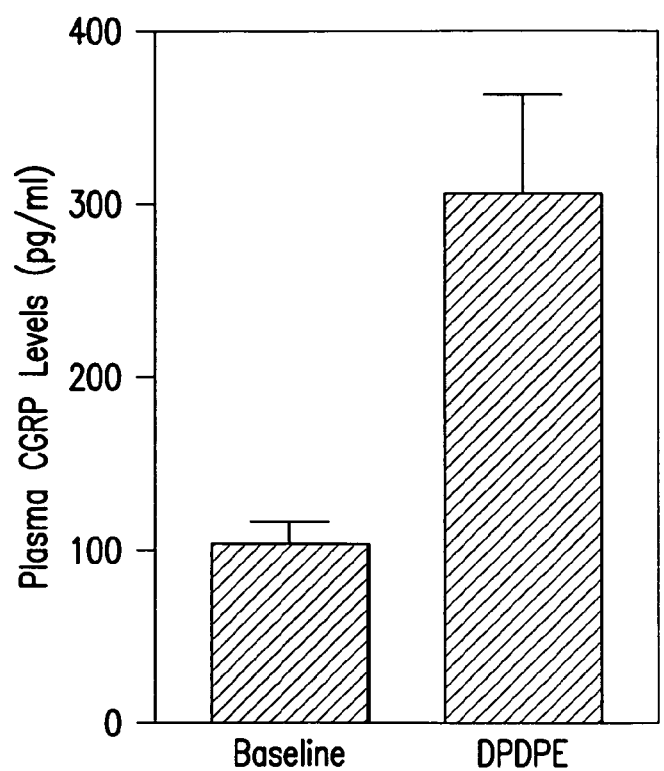
FIG. 4 shows an increase in circulating calcitonin-gene related peptide levels following intravenous administration of δ-opioid agonist DPDPE in vivo. There is about 2-fold increase in plasma calcitonin-gene related peptide levels 6-hr after DPDPE (100 pg/kg) infusion compared to the baseline levels (n=3 rats).

Consistent with calcitonin-gene related peptide gene upregulation by δ-opioid agonist, i.v. infusion of DPDPE increases circulating calcitonin-gene related peptide levels by 2 fold presumably due to increased cardiac calcitoningene related peptide spillover from intrinsic cardiac adrenergic cells (FIG. 4).

Figure 5:
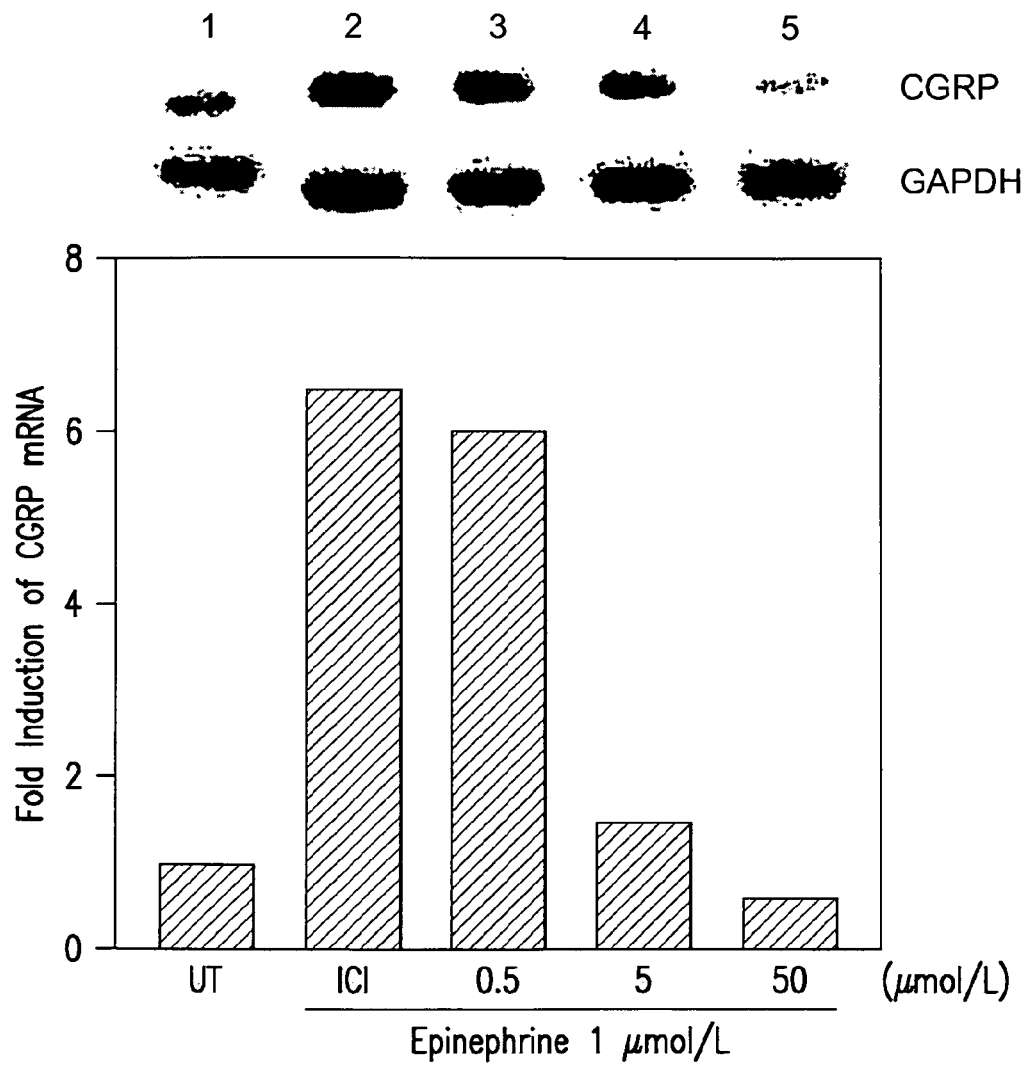
FIG. 5 shows that treatment of ICA cells with epinephrine for 1 hr increases calcitonin-gene related peptide mRNA 6-fold compared to epinephrine untreated (UT) group. Epinephrine-induced CGRP gene upregulation is attenuated in the presence of β2-adrenergic receptor antagonist ICI-118551 (ICI) in a concentration-dependent manner. ICI (at 50 µmol/L) completely eliminated epinephrine's effect on calcitonin-gene related peptide mRNA regulation. Top panels represent RT-PCR data showing upregulation of calcitonin-gene related peptide mRNA. RNA load is verified by the amount of GAPDH. Bar graphs are data normalized to their respective GAPDH mRNA.

Treatment of cultured rat ICA cells with epinephrine (1 μml/L for 1 hr), an agonist of β$_1$- and β$_2$-adrenergic receptors increases calcitonin-gene related peptide mRNA levels (FIG. 3). In the presence of β$_2$-adrenergic receptor antagonist ICI- 118551. epinephrine failed to increase calcitonin-gene related peptide mRNa levels in ICA cells (FIG. 5). This result confirms that up-regulation of calcitonin-gene related peptide mRNA in ICA cells is a specific effect mediated by $\beta_2$-adrenergic receptor.

Example 4

Infarct Size Reduction Mediated by Endogenous Cardiac CGRP

Figure 6:
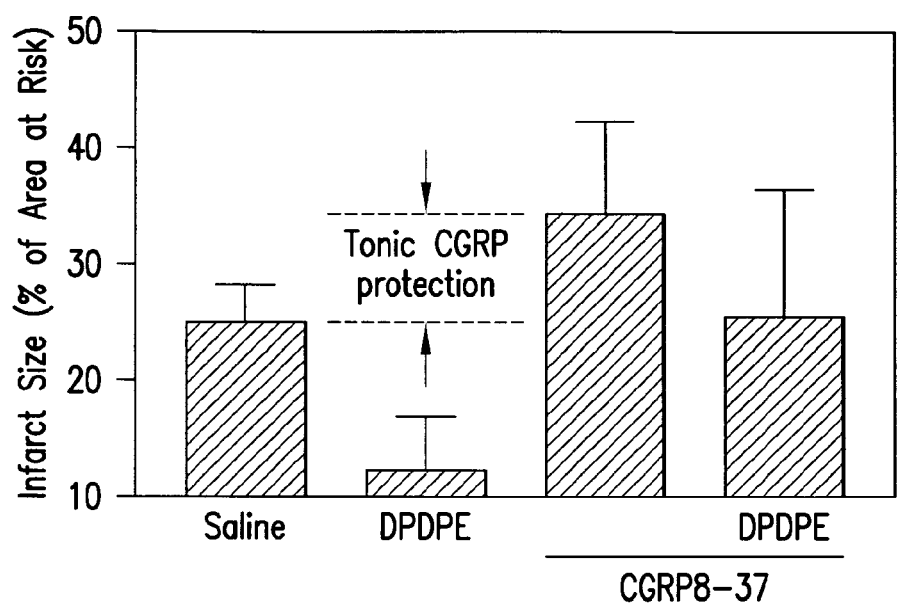
FIG. 6 shows a 38% increase in infarct size in the presence of myocardial calcitonin-gene related peptide-receptor blockade compared to the saline control group (from 25±3% to 35±8%) in a rat myocardial ischemia-reperfusion model (30-min ischemia followed by a 4-hr reperfusion). This indicates that endogenous calcitonin-gene related peptide derived from intrinsic cardiac adrenergic cells exerts tonic protection against ischemia. CGRP-receptor blockade was achieved via i.v. infusion of calcitonin-gene related peptide receptor antagonist $CGRP_{8-37}$ (10 µg kg/kg) 30 min before the onset of myocardial ischemia by ligating coronary artery. Selective δ-opioid agonist DPDPE reduced infarct size by 57% compared to the control group (25±3% vs 11±2%). However, in the presence of myocardial calcitonin-gene related peptide-receptor blockade, DPDPE-initiated infarct size reduction was markedly attenuated ($CGRP_{8-37}$+DPDPE), showing no difference compared to saline control. This indicates that δ-opioid-initiated cardioprotection is partially dependent on enhanced calcitonin-gene related peptide release as a result of intrinsic cardiac adrenergic cell activation. **:p<0.01.

In a rat myocardial infarct model, i.v. administration of calcitoningene related peptide receptor antagonist, $CGRP_{8-37}$, prior to the myocardial ischemia resulted in 38% increase in myocardial infarct size compared to control group (FIG. 6). This finding indicates that basal endogenous calcitonin-gene related peptide release from intrinsic cardiac adrenergic cells contributes significantly to cardioprotection against ischemia-reperfusion injury.

Furthermore, it was also observed that $\delta$-opioid agonist, DPDPE enhanced calcitonin-gene related peptide release from intrinsic cardiac adrenergic cells. This $\delta$-opioid-enhanced calcitonin-gene related peptide release accounted, in part, for DPDPE-initiated myocardial infarct size reduction. Apoptosis is one of the important mechanisms responsible for myocardial ischemia-reperfusion injury (Gottlieb et al., 1994; Scarabelli et al., 2006). The infarct size limiting effect exerted by endogenous calcitonin-gene related peptide derived from intrinsic cardiac adrenergic cells is presumably due to its anti-apoptotic effect.

Example 5

Histological Identification of CGRP Expression in ICA Cell

It has been traditionally assumed that cardiac CGRP is solely derived from cardiac afferent nerve endings which are only scarcely distributed to epicardial coronary arteries (Chow et al., 1993). The inventors will demonstrate the expression of CGRP immunoreactivity and CGRP mRNA in ICA cells in human and rat left ventricular myocardium.

A. Methods

Detection of CGRP immunoreactivity in ICA cells in human and rat heart. The inventors have collected 8 human LV tissue samples from surgically discarded tissue. To co-localize CGRP and TH immunoreactivity in ICA cell, the immunoreactivity will be detected and amplified by labeling with dual fluorescent chromes. Details for this method have been described previously (Huang et al., 2007). For the rat study, Sprague-Dawley adult rat heart (n=3) will be examined using the same method described for human.

Detection of in situ CGRP mRNA in human ICA cells. In situ hybridization coupled with immunofluorescent double labeling will be used to identify CGRP gene-expression in ICA cells in human heart tissue. (see FIGS. 1A-1F) The cDNA probe for human $\alpha$-CGRP mRNA is a gift from Dr. C Yallampalli's laboratory of UTMB in Galveston, Tex. (Dong et al., 2006). Paraffin sections of human LV tissue will be rehydrated and treated in microwave with citrate buffer for heat-Induced Epitope Retrieval at 100° C. for 6 min then postfixed with 2% paraformaldehyde followed by graded dehydration. FITC-labeled TH mRNA oligonucleotide probes of sense and antisense will be applied at the same concentration and sealed with Hybridization Chamber. Hybridization will be performed at 85° C. for 5 min then 2.5 h at 50° C. in the Hybrite. After post-hybridization wash, goat anti-FITC will be applied followed by donkey anti-goat IgG Alexa Fluor 594. The slides will be treated with Image-IT™ Enhancer before applying mouse anti-human TH used for labeling TH reactivity. Dual detection of chicken anti-mouse Alexa Fluor 488 and rabbit anti-mouse Alexa Fluor 488 will be performed.

Example 6

Regulation of CGRP Release and Gene Expression of ICA Cell

The inventors will determine whether ICA cells constitutively release CGRP. Furthermore, the inventors will determine whether $\delta$-opioid stimulation of ICA cells can regulate CGRP gene expression. Demonstration of regulatory mechanisms underlying CGRP synthesis and release has important implications. It paves the way for the pharmacological manipulation of endogenous CGRP mobilization exerting lasting cardiac modulation.

In vivo detection of CGRP release from human heart. CGRP release will be determined in a unique model of transplanted human heart of <5 years of post-transplantation. In this model cardiac CGRP release is exclusively derived from ICA cells, since CGRP-expressing afferent nerve endings are no longer present in human heart up to 72 months after heart transplantation (Wharton et al., 1990). Blood samples from the aorta, coronary sinus, inferior vena cava (IVC), and superior vena cava (SVC) (4-ml from each site) will be collected at the same time during the right ventricular endomyocardial biopsy (a clinical surveillance protocol for monitoring graft rejection) in post heart transplant patients (n=20) (see FIG. 5). CGRP release from ICA cells will be determined using radio-immunoassay using a commercial CGRP RIA Kit (Phoenix).

Augmenting cardiac performance by stimulation of ICA cells with $\delta$-opioid agonist. The inventors have discovered that cardiac $\delta$-opioid receptors are exclusively expressed by ICA cells (Huang et al., 2007). Since ventricular muscle cells do not express $\delta$-opioid receptors, $\delta$-opioid agonist exerts no direct effect on myocyte contractility.

Figure 10:
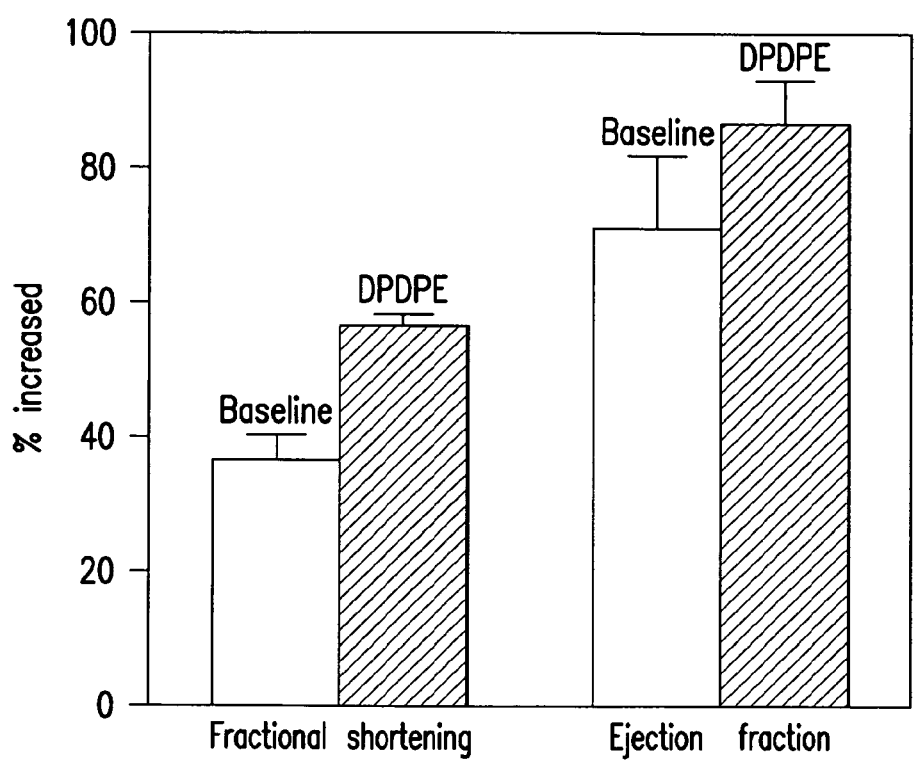
FIG. 10. shows intravenous infusion of δ-opioid agonist DPDPE (100 µg/kg) increases fractional shortening and ejection fraction by 54% and 23%, respectively in rats (n=3). The measurements were obtained from left ventricular short-axis view using echocardiography.

Stimulation of ICA cells with the $\delta$-opioid agonist such as DPDPE can enhance neurohormone (i.e., epinephrine and CGRP) release from ICA cells therefore augmenting cardiac function (positive inotropic effect). Intravenous infusion of $\delta$-opioid agonist DPDPE to rats causes sustained increase in left ventricular systolic function as reflected by increased left ventricular fractional shortening and ejection fraction (FIG. 10). The fractional shortening and ejection fraction are two clinical parameters used for evaluating left ventricular function assayed by echocardiograph. This positive inotropic effect elicited by DPDPE sustains for more than 40 minutes following drug injection. Augmenting cardiac contractile function by $\delta$-opioid receptor agonist has not been reported. $\delta$-opioid agonists can augment heart performance and can be beneficial for clinical treatment of congestive heart failure.

Example 7

Synergistic Adrenopeptidergic Anti-Ischemic Property of ICA Cell

The inventors have demonstrated that $\delta$-opioid agonist enhances adrenaline release from ICA cells resulting in potent infarct-size-reduction via myocardial $\beta_2$-AR stimulation (Huang et al., 2007). It will be interesting to see whether $\delta$-opioid agonist also enhances CGRP release from ICA cells exerting infarct-size limiting effect. Furthermore, it is important to determine whether δ-opioid stimulation leads to synergistic CGRP-adrenaline action against myocardial ischemia injury.

Experimental Myocardial Ischemia-Reperfusion Model. The rat myocardial ischemia-reperfusion model will be used (Birnbaum et al., 2005; Huang et al., 2007). This model consists of 30 min coronary artery occlusion followed by 4-hr reperfusion.

Protocol 1: To demonstrate the constitutive infarct-size-limiting effects of endogenous cardiac CGRP and epinephrine, $CGRP_1$-receptor-antagonist $CGRP_{8-37}$ (10 µg/kg), $β_2$-AR ICI-118,551(1 mg/kg), and combination of $CGRP_{8-37}$ and ICI-118,551 will be intravenously infused (0.5 ml each), respectively, 30-min before LAD ligation in three groups of rats. Saline (0.5 ml) will be infused to rats serving as control.

Protocol 2: To demonstrate the effect of δ-opioid effect on infarct size reduction, δ-opioid agonist DPDPE (100 µg/kg) will be intravenously infused to rats 20 min before LAD ligation. To determine whether δ-opioid-initiated infarct-size-reduction is partially mediated by CGRP or epinephrine, or totally dependent on synergistic action of both, DPDPE will be infused in the presence of $CGRP_{8-37}$, ICI-118,551. or the combination of $CGRP_{8-37}$ plus ICI-118,551. Each antagonist or their combination will be infused 20-min prior to DPDPE infusion. Arterial blood pressure and heart rate will be monitored continuously throughout the experiments.

Figure 7:
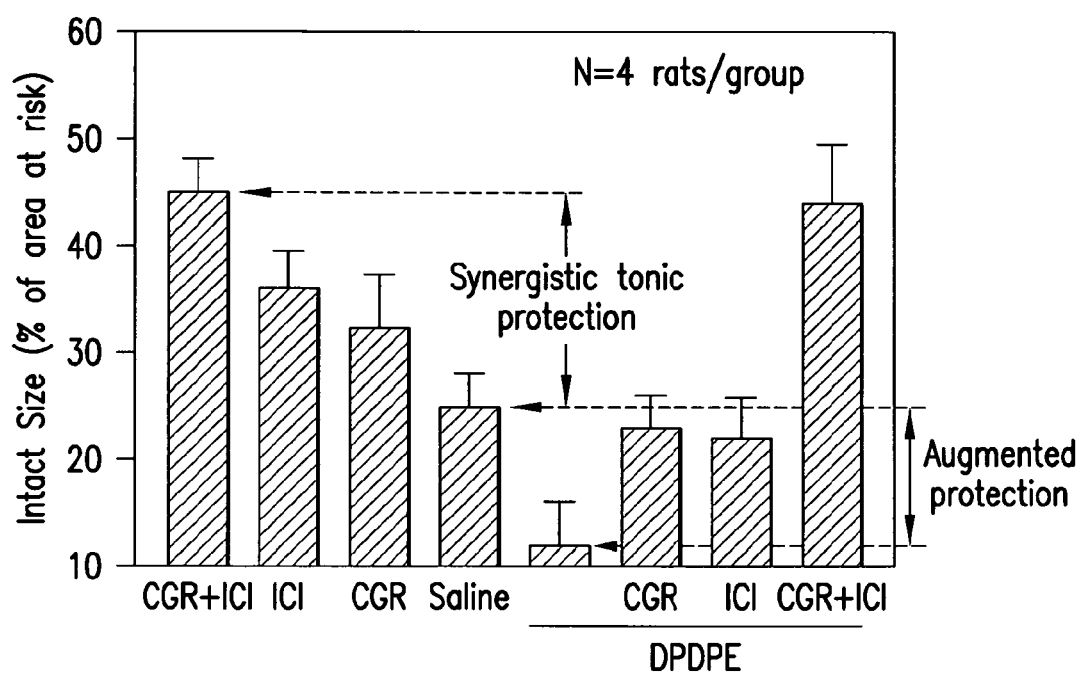
FIG. 7 shows tonic and synergistic infarct-size-limiting effect of endogenous CGRP and adrenaline at non-augmented and augmented (with δ-opioid stimulation of ICA cells) states. All the drugs including saline were intravenously infused 20-min before the onset of LAD occlusion. In the δ-opioid stimulated state, each receptor antagonist was administered 10-min before DPDPE infusion. DPDPE: δ-opioid receptor agonist. CGR: $CGRP_{8-37}$ (CGRP-receptor antagonist). ICI: ICI-118551 ($β_2$-AR antagonist).
Figure 8A:
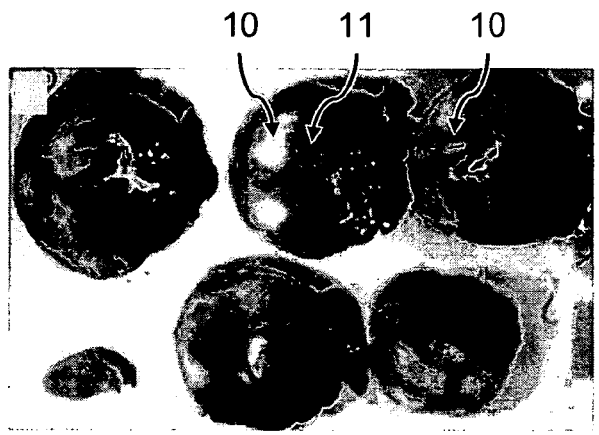
FIGS. 8A-8B shows infarct-size-reduction by the combination therapy of terbutaline (1 mg/kg) plus CGRP (30 ng/kg) intravenously co-infused 20-min after the onset of LAD occlusion. Rat MI model is created by 30-min LAD ligation followed by 4-h reperfusion. Panels 8A and 8B show infarct size (30% of area-at-risk) in rats receiving saline (control) (FIG. 8A) and combination of terbutaline (1 mg/kg)+CGRP (30 ng/kg) infused at 20-min after LAD ligation (FIG. 8B), respectively. A necrotic infarct area 10 is visible as a light gray, as is the area-at-risk 11 intermediate gray supplied by LAD. Dark zone 12 is non-risk zone supplied by right and circumflex coronary arteries.
Figure 8B:
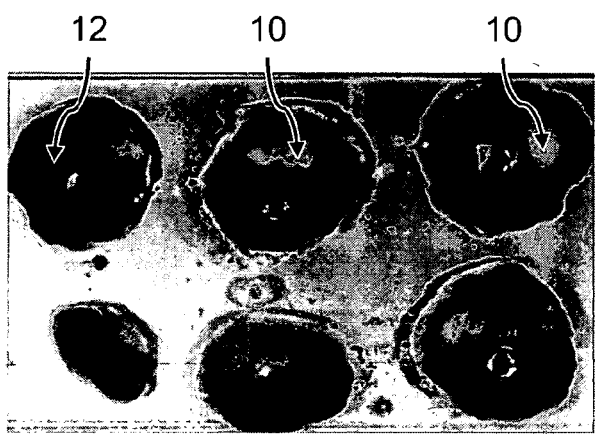
Figure 9:
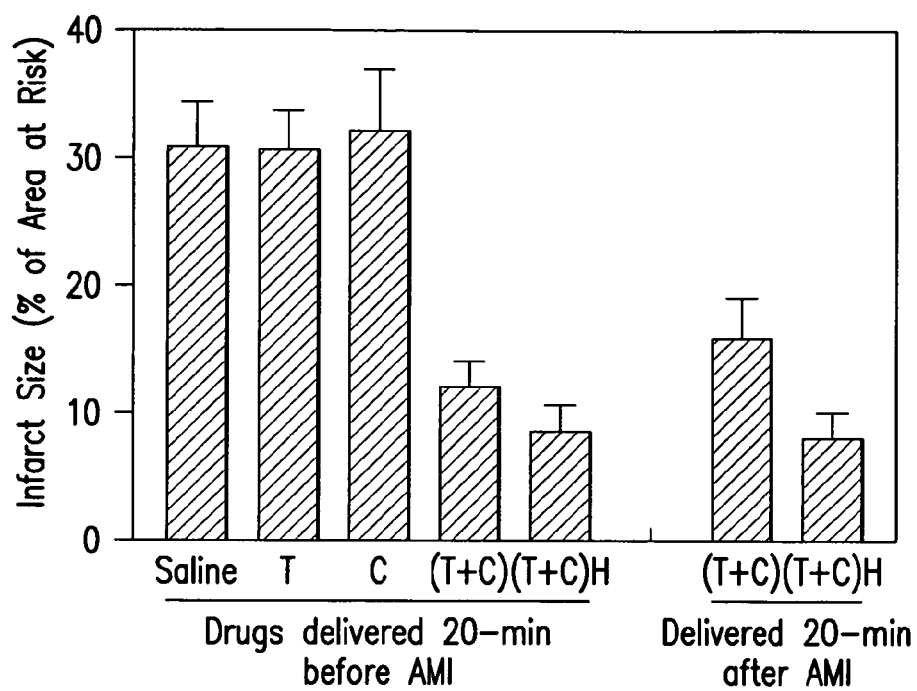
FIG. 9 shows effects of $β_2$-AR agonist terbutaline 100 µg/kg (T), CGRP 30 ng/kg (C), or their combination (T+C) on infarct size. Intravenous infusion of individual drugs before LAD ligation exerts no significant infarct-size-reduction compared to saline control. The combination therapy delivered before acute MI (AMI) confers dose-dependent infarct-size-reduction. The combination therapy delivered at 20-min after AMI also confers profound dose-dependent infarct-size-limiting effect. (T+C)H: with high dose of terbutaline 1 mg/kg.

Endogenous CGRP or epinephrine each contributes significantly to infarct-size-reduction, since blocking myocardial $CGRP_1$-receptors or $β_2$-AR each markedly increases infarct size. Simultaneous blockade of $CGRP_1$-receptors and $β_2$-AR further enhances infarct size by >90% compared to control (FIG. 9). These data indicate that endogenous CGRP and epinephrine exert synergistic tonic cardioprotection against ischemia. Furthermore, the robust infarct-size-limiting effect initiated by δ-opioid agonist is completely abolished in the presence of $β_2$-AR and $CGRP_1$-receptor blockade. This finding indicates that synergistic cardioprotection mediated by endogenous CGRP and epinephrine can be maximally augmented through δ-opioid-receptor stimulation of ICA cells (FIG. 7).

Example 8

Exogenous CGRP-β2-AR Agonist Confers Synergistic Cardioprotection

Stimulation of ICA cells with δ-opioid agonists enhances endogenous epinephrine and CGRP release resulting in synergistic $β_2$-AR-CGRP-receptor-mediated cardioprotection. $β_2$-AR agonist has have been used clinically for asthma treatment for 20 years with favorable clinical safety profile. While CGRP is still an investigational drug, it has been tested in numerous clinical trials. CGRP has a favorable clinical safety profile based on the literature. Thus, the combination therapy with $β_2$-AR agonist and CGRP may provide a readily available approach which can quickly translate basic science knowledge into clinical practice.

Methods. Terbutaline at the doses of 10 ng/kg, 100 ng/kg, and 1 mg/kg (in 0.5 ml saline) will be IV infused respectively to 3 groups of rats, 20 min before LAD occlusion. This is to determine the dose-dependent effects of terbutaline on infarct size and its side effects on hemodynamics. CGRP 10 ng/kg will be IV infused to another group of rats 20-min before LAD occlusion. The dosage of CGRP 10 ng/kg is based on previously determined one in rat MI model (Wolfrum et al., 2005). The effects of terbutaline 10 ng/kg or CGRP 10 ng/kg on infarct size will be further tested in the presence of $β_2$-AR and CGRP-receptor antagonists, respectively, with ICI-118, 551(1 mg/kg) and $CGRP_{8-37}$ (10 µg/kg). Saline (0.5 ml) will be infused to rats serving as control. (see FIG. 7)

REFERENCES

The following references, to the extent that they provide exemplary procedural or other details supplementary to those set forth herein, are specifically incorporated herein by reference.

U.S. Pat. No. 5,466,468
Almquist et al. *J. Med. Chem.*, 23:1392-1398, 1980.
Anand et al., *J. Am. Coll. Cardiol.*, 17:208-217, 1991.
Birnbaum et al., *Cardiovasc. Res.*, 65:345-355, 2005.
Brain and Grant, *Physiol. Rev.*, 84:903-934, 2004.
Chow et al., *Br. Heart J.*, 69:430-435, 1993.
Dong et al., *Am. J. Obstetrics Gynecol.*, 195:1657-1667, 2006.
Dubois-Rande et al., *Am. J. Cardiol.*, 70:906-912, 1992.
EP 45665
Freireich et al., *Cancer Chemother. Rep.*, 50:219, 1966.
Gennari et al., *Cardiovasc. Res.*, 24:239-241, 1990.
Gottlieb et al., *J Clin Invest.*, 94:1621-1628, 1994.
Gulbenkian et al., *Circ. Res.*, 73:579-588, 1993.
Hann, *J. Chem. Soc. Perkin Trans..* I 307-314, 1982.
Hasbak et al., *J. Pharmacol. Exp. Ther.*, 304:326-333, 2003.
Holladay et al., *Tetrahedron. Lett.*, 24:4401-4404, 1983.
Hruby, *Life Sci.*, 31:189-199, 1982.
Huang et al., *Am. J. Physiol.*, 276:R259-R264, 1999.
Huang et al., *Am. J. Physiol. Heart Circ. Physiol.*, 293:H376-H384, 2007.
Hudson et al., *Int. J. Pept. Prot. Res.*, 14:177-185, 1979.
Jennings-White et al., *Tetrahedron Lett.*, 23:2533, 1982.
Lefrak et al., *Cancer*, 32:302-31 4, 1973.
Lu et al., *Clin. Exper. Pharmacol. Physiol.*, 28:392-396, 2001.
Lundman et al., *Circulation*, 84:1993-2000, 1991.
Luo et al., *Eur. J. Pharmacol.*, 502:135-41, 2004.
Miyauchi et al., *Biochem. Biophys. Res. Commun.*, 155:289-294, 1988.
Morley, *Trends Pharm. Sci.*, 463-468, 1980.
Murry et al., *Circulation*, 74:1124-1136, 1986.
Nagaya et al., *Circulation*, 101:498-503, 2000.
Remington's Pharmaceutical Sciences" 15th Edition, pages 1035-1038 and 1570-1580, 1990.
Rizo and Gierasch, *Ann. Rev. Biochem.*, 61:387, 1992.
Saetrum et al., *Eur. J. Pharmacol.*, 397:373-382, 2000.
Scarabelli et al., *Curr. Prob. Cardiology,* 31:1 81 -264, 2006.
Scientific Tables, Geigy Pharmaceuticals, Ardley, N.Y., 537, 1970.
Shekhar et al., *Am. J. Cardiol.*, 67:732-736, 1991.
Spatola et al., *Life Sci.*, 38:1243-1249, 1986.
Spatola, In: *Peptide Backbone Modifications*, 1:3, 1983a.
Spatola, In: *Chemistry and Biochemistry of Amino Acids, Peptides, and Proteins*, Weinstein (Ed.), Marcel Dekker, NY, 267, 1983b.
Staat et al., *Circulation*, 112:2143-2148, 2005.
Sueur et al., *J. Mol. Cell Cardiol.*, 39:955-963, 2005.
Tokudome et al., *Endocrinology,* 143:3515-3521, 2002.
Uren et al., *Cardiovasc. Res.*, 27:1477-1481, 1993.
Van Gelderen et al., *Eur. J. Pharmacol.*, 284:51-60, 1995.
Vinten-Johansen et al., *Circulation*, 112:2085-2088, 2005.
Wharton et al., *Circ. Res.*, 66:900-912, 1990.
Wolfrum et al., *Regul. Pept.*, 127:217-224, 2005.

The invention claimed is:

1. A method of treating reperfusion injury in a subject in need thereof, comprising intravascularly administering a composition comprising the combination of the β-2-adrenergic receptor agonist terbutaline and of a calcitonin gene-related peptide (CGRP) to reduce reperfusion injury.

2. The method of claim 1, wherein reperfusion injury is cardiac tissue infarction.

3. The method of claim 1, wherein the β2-adrenergic receptor agonist is administered at a dose of 1 µg/kg to 500 µg/kg.

4. The method of claim 1, wherein the CGRP is administered at a dose of 0.1 ng/kg to 100 ng/kg.

5. The method of claim 1, wherein the step of administering is performed prior to and/or subsequent to reperfusion or reperfusion therapy.

6. The method of claim 1, wherein the β2-adrenergic receptor agonist and the CGRP are administered separately.

7. The method of claim 1, wherein the β2-adrenergic receptor agonist and the CGRP are administered in a single formulation.

8. The method of claim 1, wherein the β2-adrenergic receptor agonist and the CGRP are administered within 1 hour after ischemia.

9. The method of claim 8, wherein the β2-adrenergic receptor agonist terbutaline and the CGRP are administered 30 minutes after ischemia.

10. The method of claim 1, wherein the composition is administered by an intracoronary route.

* * * * *

SEQUENCE LISTING

<160> NUMBER OF SEQ ID NOS: 1

<210> SEQ ID NO 1
<211> LENGTH: 53
<212> TYPE: PRT
<213> ORGANISM: Homo sapiens

<400> SEQUENCE: 1

```
Arg Ile Ile Ala Gln Lys Arg Ala Cys Asp Thr Ala Thr Cys Val Thr
1               5                   10                  15

His Arg Leu Ala Gly Leu Leu Ser Arg Ser Gly Gly Val Val Lys Asn
            20                  25                  30

Asn Phe Val Pro Thr Asn Val Gly Ser Lys Ala Phe Gly Arg Arg Arg
        35                  40                  45

Arg Asp Leu Gln Ala
    50
```